United States Patent [19]

Hipskind et al.

[11] Patent Number: 5,773,441
[45] Date of Patent: Jun. 30, 1998

[54] 2-ACYLAMINOPROPANAMIDES AS GROWTH HORMONE SECRETAGOGUES

[75] Inventors: Philip Arthur Hipskind, New Palestine; Jeffrey Alan Dodge, Indianapolis, both of Ind.

[73] Assignee: Eli Lilly and Company, Indianapolis, Ind.

[21] Appl. No.: 700,206

[22] Filed: Aug. 20, 1996

Related U.S. Application Data

[60] Provisional application No. 60/002,579, Aug. 21, 1995.
[51] Int. Cl.$^6$ .......................... A61K 31/495; A61K 31/50; A61K 31/445
[52] U.S. Cl. ............................................. 514/253; 514/316
[58] Field of Search ...................................... 514/316, 253

[56] References Cited

U.S. PATENT DOCUMENTS 5,565,568   10/1996   Cho et al. ................................. 544/373

*Primary Examiner*—Marianne M. Cintins
*Assistant Examiner*—M. Moezie
*Attorney, Agent, or Firm*—Paul J. Gaylo; David E. Boone

[57] ABSTRACT

This invention provides a series of novel substituted propanamides which are useful in the a physiological condition which may be modulated by an increase in growth hormone. This invention also provides methods for the treatment of such physiological conditions which comprise administering a growth hormone secretagogue as described in the present invention in combination with growth hormone releasing hormone.

9 Claims, No Drawings

2-ACYLAMINOPROPANAMIDES AS GROWTH HORMONE SECRETAGOGUES

PRIORITY CLAIM

This application claims the benefit of U.S. provisional application Ser. No. 60/002579, filed Aug. 21, 1995.

BACKGROUND OF THE INVENTION

Growth hormone is a secretory protein of the pituitary gland of animals having wide ranging developmental effects on the organism. Artificial manipulation of growth hormone levels has been demonstrated to have significant therapeutic utility. Human growth hormone supplementation has been shown to be an effective treatment for growth hormone deficiencies and their related disease states in humans. Apart from this application, studies have uncovered new and significant properties of growth hormone which lend further importance to the ability to control growth hormone levels. For example, recent clinical studies indicate that growth hormone supplementation may be useful in combating the maladies of aging in humans. Elevated growth hormone levels in animals have been shown to result in increased lean muscle mass. One application of this latter observation could result in higher production of leaner meat products or in the production of larger and/or stronger animals.

While growth hormone is naturally produced by the pituitary gland, the secretion of growth hormone into the bloodstream is controlled by a second protein, Growth Hormone Releasing Factor (GRF). This hormone is also commonly known in the art as somatocrinin, Growth Hormone Releasing Hormone (GHRH), and Growth Releasing Hormone (GRH).

There are two ways to approach the problem of increasing circulating levels of growth hormone: (1) increase the level of human growth hormone in the organism directly or (2) increase the organisms natural tendency to produce growth hormone. The latter strategy may be achieved via supplementation with GRF. GRF has been demonstrated to increase the circulatory levels of growth hormone in vivo. Rivier, et al., *Nature* (London), 300:276 (1982). The effect of GRF (and various structural analogs thereof) on growth hormone production has been widely studied. A primary obstacle to the use of GRF as a direct supplement is its short lifespan in vivo. L. A. Frohman, et al., *Journal of Clinical Investigation*, 78:906 (1986). More potent and/or longer lasting GRF molecules are therefore desirable for the development of effective human therapeutic or animal husbandry agents.

The structure of GRF has been modified in numerous ways resulting in longer lasting and/or more potent GRF analogs. It has been demonstrated that the first 29 amino acids from the N-terminus are sufficient to retain full GRF activity. Speiss, et al., *Biochemistry*, 21:6037 (1982). One strategy has been the incorporation of novel D-amino acid residues in various regions of the GRF molecule. V. A. Lance, et al., *Biochemical and Biophysical Research Communications*, 119:265 (1984); D. H. Coy, et al., *Peptides*, 8(suppl. 1):49 (1986). Another strategy has modified the peptide backbone of GRF by the incorporation of peptide bond isosteres in the N-terminal region. D. Tourwe, *Janssen. Chim. Acta*, 3:3 (1985); S. J. Hocart, et al., *Journal of Medicinal Chemistry*, 33:1954–58 (1990). A series of very active analogs of GHRH is described in European Patent Publication 511,003, published Oct. 28, 1992.

In addition to the actions of GHRH there are various ways known to release growth hormone. For example, chemicals such as arginine, L-3,4-dihydroxyphenylalanine (L-DOPA), glucagon, vasopressin, and insulin-induced hypoglycemia, as well as activities such as sleep and exercise, indirectly cause growth hormone to be released from the pituitary by acting in some fashion on the hypothalamus, perhaps either to decrease somatostatin secretion or to increase the secretion of GHRH.

In cases where increased levels of growth hormone are desired, the problem has generally been solved by providing exogenous growth hormone or by administering GHRH, or a related peptidyl compounds which stimulates growth hormone production or release. In either instance the peptidyl nature of the compound has necessitated that it be administered by injection.

Other compounds have been developed which stimulate the release of endogenous growth hormone, such as analogous peptidyl compounds related to GHRH. These peptides, while considerably smaller than growth hormones are still susceptible to metabolic instability.

Administration of the hexapeptide growth hormone releasing peptide-6 (GHRP-6) results in the secretion of growth hormone in many species, including humans. This peptide has the following sequence.

His-D-Trp-Ala-Trp-D-Phe-Lys-NH$_2$

This peptide is one of a series of synthetic peptides, the structures of which were based on the pentapeptide Met-enkephalin. It has been shown that GHRP binds specifically to the pituitary, although the binding does not involve the opioid, GHRH, or the somatostatin receptors.

In recent years significant efforts have been taken to develop nonpeptidyl analogs of this series of compounds. Such compounds, termed growth hormone secretagogues, should be orally bioavailable, induce the production or release of growth hormone, and act synergistically with GHRH.

Representative growth hormone secretagogues are disclosed in U.S. Pat. No. 3,239,345; U.S. Pat. No. 4,036,979; U.S. Pat. No. 4,411,890; U.S. Pat. No. 5,206,235; U.S. Pat. No. 5,248,841; U.S. Pat. No. 5,310,737; U.S. Pat. No. 5,310,017; European Patent Publication 144,230; European Patent Publication 513,974; Patent Cooperation Treaty Patent Publication WO 94/07486; Patent Cooperation Treaty Patent Publication WO 94/08583; Patent Cooperation Treaty Patent Publication WO 94/13696; and *Science*, 260:1640–1643 (1993), the entire of all of which are herein incorporated by reference.

U.S. Pat. No. 5,206,235, issued Apr. 27, 1993, describes a series of benzolactam compounds typified by the following structure.

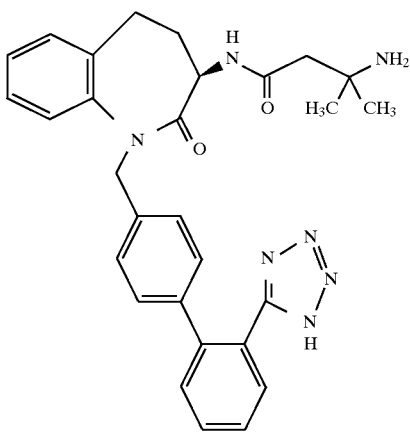

These compounds have demonstrated clinical activity in humans in raising the growth hormone secretory levels. B. J. Gertz, *Journal of Clinical Endocrinology and Metabolism*, 77:1393–1397 (1993).

A second generation of growth hormone secretagogues is described in Patent Cooperation Treaty Patent Publication WO 94/13696, published Jun. 23, 1994. These compounds are typified by the following two structures.

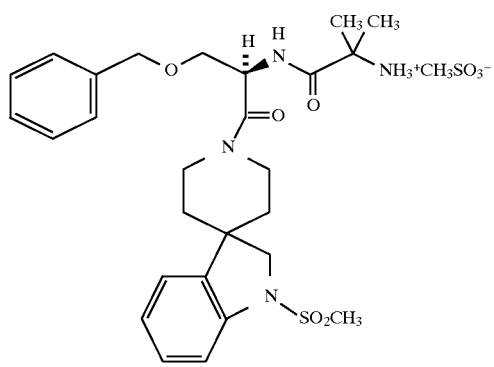

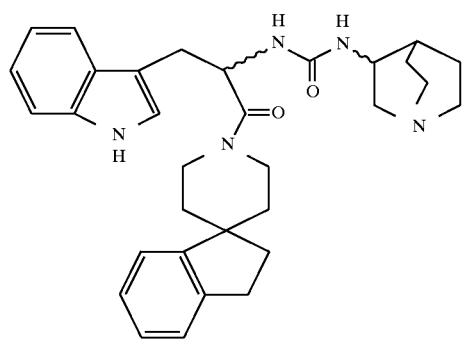

The present invention provides a series of compounds that have activity as growth hormone secretagogues. These compounds are orally active and non-peptidyl in nature and are, therefore, more metabolically stable than growth hormone, growth hormone releasing hormone, or analogs of either of these proteins. The compounds employed in the present invention are preferred for human pharmaceutical uses as well as veterinary uses, particularly in cattle, swine, sheep, poultry and fish.

SUMMARY OF THE INVENTION

This invention encompasses methods for the treatment or prevention of a physiological condition which may be modulated by an increase in growth hormone, which method comprises administering to an animal in need of said treatment an effective amount of a compound of Formula I

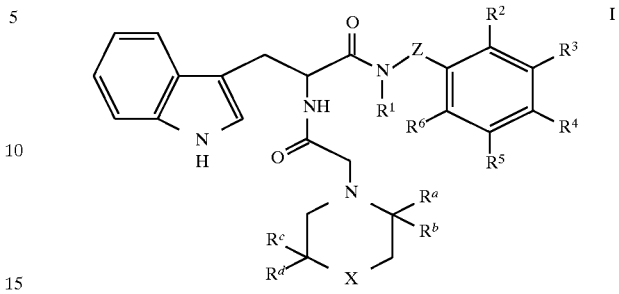

wherein:

$R^1$ is hydrogen, $C_1$–$C_6$ alkyl, or $C_2$–$C_6$ alkanoyl;

$R^2$, $R^3$, $R^4$, $R^5$, and $R^6$ are independently selected from the group consisting of hydrogen, halo, $C_1$–$C_6$ alkyl, $C_1$–$C_6$ alkoxy, $C_1$–$C_6$ alkylamino, $C_1$–$C_6$ alkylthio, amino, and trifluoromethyl;

$R^a$ and $R^b$ are each hydrogen or together form an oxo group;

$R^c$ and $R^d$ are each hydrogen or together form an oxo group;

Z is a bond or $C_1$–$C_6$ alkylidenyl; and

X is

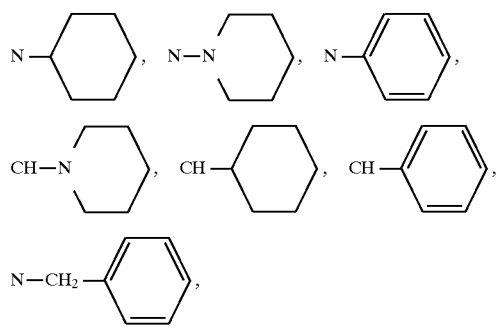

N—$R^7$, CH—$NR^8R^9$, or CH—$R^{10}$ where $R^7$, $R^8$, $R^9$, and $R^{10}$ are independently selected from the group consisting of hydrogen and $C_1$–$C_6$ alkyl;

or a pharmaceutically acceptable salt or solvate thereof.

In another embodiment, this invention provides methods for the treatment or prevention of a physiological condition which may be modulated by an increase in growth hormone, which method comprises administering to an animal in need of said treatment an effective amount of a compound of Formula I in combination with growth hormone releasing factor, or an analog thereof.

DETAILED DESCRIPTION AND PREFERRED EMBODIMENTS

The terms and abbreviations used in the instant examples have their normal meanings unless otherwise designated. For example "°C." refers to degrees Celsius; "N" refers to normal or normality; "mmol" refers to millimole or millimoles; "g" refers to gram or grams;

"ml" means milliliter or milliliters; "M" refers to molar or molarity;

"MS" refers to mass spectrometry; "FDMS" refers to field desorption mass spectrometry; "UV" refers to ultraviolet spectroscopy; "IR" refers to infrared spectroscopy; and "NMR" refers to nuclear magnetic resonance spectroscopy.

As used herein, the term "$C_1$–$C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "$C_1$–$C_6$ alkyl" includes within its definition the term "$C_1$–$C_4$ alkyl".

"Halo" represents chloro, fluoro, bromo or iodo.

"$C_1$–$C_6$ alkylthio" represents a straight or branched alkyl chain having from one to six carbon atoms attached to a sulfur atom.

Typical $C_1$–$C_6$ alkylthio groups include methylthio, ethylthio, propylthio, isopropylthio, butylthio and the like. The term "$C_1$–$C_6$ alkylthio" includes within its definition the term "$C_1$–$C_4$ alkylthio".

"$C_1$–$C_6$ alkylamino" represents a straight or branched alkylamino chain having from one to six carbon atoms attached to an amino group. Typical $C_1$–$C_6$ alkyl-amino groups include methylamino, ethylamino, propylamino, isopropylamino, butylamino, sec-butylamino and the like.

$C_1$–$C_6$ alkoxy" represents a straight or branched alkyl chain having from one to six carbon atoms attached to an oxygen atom.

Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term ° $C_1$–$C_4$ alkoxy".

"$C_2$–$C_6$ alkanoyl" represents a straight or branched alkyl chain having from one to five carbon atoms attached through a carbonyl moiety. Typical $C_2$–$C_6$ alkanoyl groups include ethanoyl (also referred to as acetyl), propanoyl, isopropanoyl, butanoyl, t-butanoyl, pentanoyl, hexanoyl, and the like.

"$C_1$–$C_6$ alkylidenyl" refers to a straight or branched, divalent, saturated aliphatic chain of one to six carbon atoms and includes, but is not limited to, methylenyl, ethylenyl, propylenyl, isopropylenyl, butylenyl, isobutylenyl, t-butylenyl, pentylenyl, isopentylenyl, hexylenyl, and the like.

The term "heterocycle" represents a stable 5- to 7-membered monocyclic or 7- to 10-membered bicyclic heterocyclic ring which is saturated or unsaturated and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure.

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; benzoylmethylsulfonyl group, 2-nitrophenylsulfenyl, diphenylphosphine oxide and like amino-protecting groups. The species of amino-protecting group employed is usually not critical so long as the derivatized amino group is stable to the condition of subsequent reactions on other positions of the intermediate molecule and can be selectively removed at the appropriate point without disrupting the remainder of the molecule including any other amino-protecting groups. Preferred amino-protecting groups are trityl, t-butoxycarbonyl (t-BOC), allyloxycarbonyl and benzyloxycarbonyl. Further examples of groups referred to by the above terms are described by E. Haslam, PROTECTIVE GROUPS IN ORGANIC CHEMISTRY, (J. G. W. McOmie, ed., 1973), at Chapter 2; and T. W. Greene and P. G. M. Wuts, PROTECTIVE GROUPS IN ORGANIC SYNTHESIS (1991), at Chapter 7.

The term "leaving group" as used herein refers to a group of atoms that is displaced from a carbon atom by the attack of a nucleophile in a nucleophilic substitution reaction. The term "leaving group" as used in this document encompasses, but is not limited to, activating groups.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and may be, for example, succinimidoxy, phthalimidoxy, benzotriazolyloxy, benzenesulfonyloxy, methanesulfonyloxy, toluenesulfonyloxy, azido, or —O—CO—($C_4$–$C_7$ alkyl).

The term "haloformate" as used herein refers to an ester of a haloformic acid, this compound having the formula

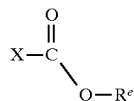

wherein X is halo, and $R^e$ is $C_1$–$C_6$ alkyl. Preferred haloformates are bromoformates and chloroformates. Especially preferred are chloroformates. Those haloformates wherein $R^3$ is $C_3$–$C_6$ alkyl are preferred. Most preferred is isobutyl chloroformate.

The compounds used in the method of the present invention may have one or more asymmetric centers. As a consequence of these chiral centers, the compounds of the present invention occur as racemates, mixtures of enantiomers and as individual enantiomers, as well as diastereomers and mixtures of diastereomers. All asymmetric forms, individual isomers and combinations thereof, are within the scope of the present invention. The terms "R" and "S" are used herein as commonly used in organic chemistry to denote specific configuration of a chiral center.

The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in NOMENCLATURE OF ORGANIC COMPOUNDS: PRINCIPLES AND PRACTICE, (J. H. Fletcher, et al., eds., 1974) at pages 103–120.

In addition to the (R)-(S) system, the older D-L system is also used in this document to denote absolute configuration, especially with reference to amino acids. In this system a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

In order to preferentially prepare one optical isomer over its enantiomer, the skilled practitioner can proceed by one of two routes. The practitioner may first prepare the mixture of enantiomers and then separate the two enantiomers. A commonly employed method for the resolution of the racemic mixture (or mixture of enantiomers) into the individual enantiomers is to first convert the enantiomers to diastereomers by way of forming a salt with an optically active acid or base. These diastereomers can then be separated using differential solubility, fractional crystallization, chromatography, or like methods.

Further details regarding resolution of enantiomeric mixtures can be found in J. Jacques, et al., ENANTIOMERS, RACEMATES, AND RESOLUTIONS, (1991).

In addition to the schemes described above, the practitioner of this invention may also choose an enantiospecific protocol for the preparation of the compounds of Formula I. Such a protocol employs a synthetic reaction design which maintains the chiral center present in the starting material in a desired orientation. These reaction schemes usually produce compounds in which greater than 95 percent of the title product is the desired enantiomer.

As noted supra, this invention encompasses methods employing the pharmaceutically acceptable salts of the compounds defined by Formula I. Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, y-hydroxybutyrate, glycollate, tartrate, methanesulfonate, propanesulfonate, naphthalene-1-sulfonate, naphthalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Salts of amine groups may also comprise quaternary ammonium salts in which the amino nitrogen carries a suitable organic group such as an alkyl, alkenyl, alkynyl, or aralkyl moiety.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

This invention further eencompasses methods employing pharmaceutically acceptable solvates of the compounds of Formulas I. Many of the Formula I compounds can combine with solvents such as water, methanol, ethanol and acetomtrile to form pharmaceutically acceptable solvates such as the corresponding hydrate, methanolate, ethanolate and acetonitrilate.

This invention also encompasses methods employing the pharmaceutically acceptable prodrugs of the compounds of Formula I.

A prodrug is a drug which has been chemically modified and may be biologically inactive at its site of action, but which may be degraded or modified by one or more enzymatic or other in vivo processes to the parent bioactive form. This prodrug should have a different pharmacokinetic profile than the parent, enabling easier absorption across the mucosal epithelium, better salt formation or solubility, or improved systemic stability (an increase in plasma half-life, for example).

Typically, such chemical modifications include:
1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form;

or any combination of 1 to 3, supra. Conventional procedures for the selection and preparation of suitable prodrug derivatives are described, for example, in H. Bundgaard, DESIGN OF PRODRUGS, (1985).

The preferred methods of the present invention employ the preferred compounds of the present invention. The preferred compounds of the present invention are those compounds in which:

(i) Z is a bond, methylenyl, or ethylenyl;

(ii) at least one, but not more than three, of $R^2$, $R^3$, $R^4$, $R^5$, and $R^6$ are independently selected from the group consisting of chloro, fluoro, trifluoromethyl, methyl, ethyl, methoxy, ethoxy, methylamine, ethylamine, amino, methylthio, and ethylthio;

(iii) $R^1$ is hydrogen, methyl, or acetyl; and (iv) X, when combined with the heterocyclic group to which it is attached forms 4-cyclohexylpiperazinyl, 4-(piperidin-1-yl)piperidin-1-yl, 4-phenylpiperazin-1-yl, 4-phenylpiperidin-1-yl, 4-dimethylaminopiperidin-1-yl, 4-diethylaminopiperidin-1-yl, 4-benzylpiperazin-1-yl, (4-methyl)-2,5-dioxopiperazin-1-yl, (4-phenyl)-2,5-dioxopiperazin-1-yl, (4-benzyl)-2,5-dioxopiperazin-1-yl; or a pharmaceutically acceptable salt, solvate, or prodrug of any such compound.

Especially preferred compounds include N-(2-methoxybenzyl)-3-(1H-indol-3-yl)-2-[[(4-phenylpiperazin-1-yl)acetyl]amino]propanamide, N-(2-ethoxybenzyl)-3-(1H-indol-3-yl)-2-[[(4-phenylpiperazin-1-yl)acetyl]aminolpropanamide, N-(2-methylbenzyl)-3-(1H-indol-3-yl)-2-[[(4-phenylpiperazin-1-yl)acetyl]amino]propanamide, N-(2-chlorobenzyl)-3-(1H-indol-3-yl)-2-[[(4-phenylpiperazin-1-yl)acetyl]amino]propanamide, N-(2-trifluoromethylbenzyl)-3-(1H-indol-3-yl)-2-[[(4-phenylpiperazin-1-yl)acetyl]amino]propanamide, N-(2-ethylbenzyl)-3-(1H-indol-3-yl)-2-[[(4-phenylpiperazin-1-yl)acetyl]amino]propanamide, N-(3,4-dimethoxybenzyl)-3-(1H-indol-3-yl)-2-[[(4-phenylpiperazin-1-yl)acetyl]amino]propanamide, N-(3,4-dimethylbenzyl)-3-(1H-indol-3-yl)-2-[[(4-phenylpiperazin-1-yl)acetyl]amino]propanamide, N-(3,4-diethoxybenzyl)-3-(1H-indol-3-yl)-2-[[(4-phenylpiperazin-1-yl)acetyl]amino]propanamide, N-(3,4-diethylbenzyl)-3-(1H-indol-3-yl)-2-[[(4-phenylpiperazin-1-yl)acetyl]amino]propanamide, N-(3,4-dichlorobenzyl)-3-(1H-indol-3-yl)-2-[[(4-phenylpiperazin-1-yl)acetyl]amino]propanamide, N-[3,4-bis(trifluoromethyl)benzyl]-3-(1H-indol-3-yl)-2-[[(4-phenylpiperazin-1-yl)acetyl]amino]propanamide, N-(3,4,5-trimethoxybenzyl)-3-(1H-indol-3-yl)-2-[[(4-phenylpiperazin-1-yl)acetyl]amino]propanamide, N-(3,4,5-trimethylbenzyl)-3-(1H-indol-3-yl)-2-[[(4-phenylpiperazin-1-yl)acetyl]amino]propanamide, N-(3,4,5-triethoxybenzyl)-3-(1H-indol-3-yl)-2-[[(4-phenylpiperazin-1-yl)acetyl]amino]propanamide, N-(3,4,5-triethylbenzyl)-3-(1H-indol-3-yl)-2-[[(4-phenylpiperazin-1-yl)acetyl]amino]propanamide, N-(3,4,5-trichlorobenzyl)-3-(1H-indol-3-yl)-2-[[(4-phenylpiperazin-1-yl)acetyl]amino]propanamide, N-[3,4,5-tri(trifluoromethyl)benzyl]-3-(1H-indol-3-yl)-2-[[(4-phenylpiperazin-1-yl)acetyl]amino]propanamide, N-(2-methoxybenzyl)-3-(1H-indol-3-yl)-2-[[(4-cyclohexylpiperazin-1-yl)acetyl]amino]propanamide, N-(2-ethoxybenzyl)-3-(1H-indol-3-yl)-2-[[(4-cyclohexylpiperazin-1-yl)acetyl]amino]propanamide, N-(2-methylbenzyl)-3-(1H-indol-3-yl)-2-[[(4-cyclohexylpiperazin-1-yl)acetyl]amino]propanamide, N-(2-chlorobenzyl)-3-(1H-indol-3-yl)-2-[[(4-cyclohexylpiperazin-1-yl)acetyl]amino]propanamide, N-(2-trifluoromethylbenzyl)-3-(1H-indol-3-yl)-2-[[(4-cyclohexylpiperazin-1-yl)acetyl]amino]propanamide, N-(2-ethylbenzyl)-3-(1H-indol-3-yl)-2-[[(4-cyclohexylpiperazin-1-yl)acetyl]amino]propanamide, N-(3,4-dimethoxybenzyl)-3-(1H-indol-3-yl)-2-[[(4-cyclohexylpiperazin-1-yl)acetyl]amino]propanamide, N-(3,4-dimethylbenzyl)-3-(1H-indol-3-yl)-2-[[(4-cyclohexylpiperazin-1-yl)acetyl]amino]propanamide, N-(3,4-diethoxybenzyl)-3-(1H-indol-3-yl)-2-[[(4-cyclohexylpiperazin-1-yl)acetyl]amino]propanamide, N-(3,4-diethylbenzyl)-3-(1H-indol-3-yl)-2-[[(4-cyclohexylpiperazin-1-yl)acetyl]amino]propanamide, N-(3,4-dichlorobenzyl)-3-(1H-indol-3-yl)-2-[[(4-cyclohexylpiperazin-1-yl)acetyl]amino]propanamide, N-[3,5-bis(trifluoromethyl)benzyl]-3-(1H-indol-3-yl)-2-[[(4-cyclohexylpiperazin-1-yl)acetyl]amino]propanamide, N-(3,4,5-trimethoxybenzyl)-3-(1H-indol-3-yl)-2-[[(4-cyclohexylpiperazin-1-yl)acetyl]amino]propanamide, N-(3,4,5-trimethylbenzyl)-3-(1H-indol-3-yl)-2-[[(4-cyclohexylpiperazin-1-yl)acetyl]amino]propanamide, N-(3,4,5-triethoxybenzyl)-3-(1H-indol-3-yl)-2-[[(4-cyclohexylpiperazin-1-yl)acetyl]amino]propanamide, N-(3,4,5-triethylbenzyl)-3-(1H-indol-3-yl)-2-[[(4-cyclohexylpiperazin-1-yl)acetyl]amino]propanamide, N-(3,4,5-trichlorobenzyl)-3-(1H-indol-3-yl)-2-[[(4-cyclohexylpiperazin-1-yl)acetyl]amino]propanamide, N-[3,4,5-tri(trifluoromethyl)benzyl]-3-(1H-indol-3-yl)-2-[[(4-cyclohexylpiperazin-1-yl)acetyl]amino]propanamide, N-(2-methoxybenzyl)-3-(1H-indol-3-yl)-2-[[[4-(piperidin-1-yl)piperidin-1-yl]acetyl]amino]propanamide, N-(2-ethoxybenzyl)-3-(1H-indol-3-yl)-2-[[[4-(piperidin-1-yl)piperidin-1-yl]acetyl]amino]propanamide, N-(2-methylbenzyl)-3-(1H-indol-3-yl)-2-[[[4-(piperidin-1-yl)piperidin-1-yl]acetyl]amino]propanamide, N-(2-chlorobenzyl)-3-(1H-indol-3-yl)-2-[[[4-(piperidin-1-yl)piperidin-1-yl]acetyl]amino]propanamide, N-(2-trifluoromethylbenzyl)-3-(1H-indol-3-yl)-2-[[[4-(piperidin-1-yl)piperidin-1-yl]acetyl]amino]propanamide, N-(2-ethylbenzyl)- 3-(1H-indol-3-yl)-2-[[[4-(piperidin-1-yl)piperidin-1-yl]acetyl]amino]propanamide, N-(3,4-dimethoxybenzyl)-3-(1H-indol-3-yl)-2-[[[4-(piperidin-1-yl)piperidin-1-yl]acetyl]amino]propanamide, N-(3,4-dimethylbenzyl)-3-(1H-indol-3-yl)-2-[[[4-(piperidin-1-yl)piperidin-1-yl]acetyl]amino]propanamide, N-(3,4-diethoxybenzyl)-3-(1H-indol-3-yl)-2-[[[4-(piperidin-1-yl)piperidin-1-yl]acetyl]amino]propanamide, N-(3,4-diethylbenzyl)-3-(1H-indol-3-yl)-2-[[[4-(piperidin-1-yl)piperidin-1-yl]acetyl]amino]propanamide, N-(3,4-dichlorobenzyl)-3-(1H-indol-3-yl)-2-[[[4-(piperidin-1-yl)piperidin-1-yl]acetyl]amino]propanamide, N-[3,5-bis(trifluoromethyl)benzyl]-3-(1H-indol-3-yl)-2-[[[4-(piperidin-1-yl)piperidin-1-yl]acetyl]amino]propanamide, N-(3,4,5-trimethoxybenzyl)-3-(1H-indol-3-yl)-2-[[[4-(piperidin-1-yl)piperidin-1-yl]acetyl]amino]propanamide, N-(3,4,5-trimethylbenzyl)-3-(1H-indol-3-yl)-2-[[[4-(piperidin-1-yl)piperidin-1-yl]acetyl]amino]propanamide, N-(3,4,5-triethoxybenzyl)-3-(1H-indol-3-yl)-2-[[[4-(piperidin-1-yl)piperidin-1-yl]acetyl]amino]propanamide, N-(3,4,5-triethylbenzyl)-3-(1H-indol-3-yl)-2-[[[4-(piperidin-1-yl)piperidin-1-yl]acetyl]amino]propanamide, N-(3,4,5-trichlorobenzyl)-3-(1H-indol-3-yl)-2-[[[4-(piperidin-1-yl)piperidin-1-yl]acetyl]amino]propanamide, N-[3,4,5-tri(trifluoromethyl)benzyl]-3-(1H-indol-3-yl)-2-[[[4-(piperidin-1-yl)piperidin-1-yl]acetyl]amino]propanamide, N-(2-methoxybenzyl)-N-acetyl-3-(1H-indol-3-yl)-2-[[(4-phenylpiperazin-1-yl)acetyl]amino]propanamide, N-(2-ethoxybenzyl)-N-acetyl-3-(1H-indol-3-yl)-2-[[(4-phenylpiperazin-1-yl)acetyl]amino]propanamide, N-(2-methylbenzyl)-N-acetyl-3-(1H-indol-3-yl)-2-[[(4-phenylpiperazin-1-yl)acetyl]amino]propanamide, N-(2- chlorobenzyl)-N-acetyl-3-(1H-indol-3-yl)-2-[[(4-phenylpiperazin-1-yl)acetyl]amino]propanamide, N-(2-trifluoromethylbenzyl)-N-acetyl-3-(1H-indol-3-yl)-2-[[(4-phenylpiperazin-1-yl)acetyl]amino]propanamide,N-(2-ethylbenzyl)-N-acetyl-3-(1H-indol-3-yl)-2-[[(4-phenylpiperazin-1-yl)acetyl]amino]propanamide, N-(3,4-dimethoxybenzyl)-N-acetyl-3-(1H-indol-3-yl)-2-[[(4-phenylpiperazin-1-yl)acetyl]amino]propanamide, N-(3,4-dimethylbenzyl)-N-acetyl-3-(1H-indol-3-yl)-2-[[(4-phenylpiperazin-1-yl)acetyl]amino]propanamide, N-(3,4-diethoxybenzyl)-N-acetyl-3-(1H-indol-3-yl)-2-[[(4-phenylpiperazin-1-yl)acetyl]amino]propanamide, N-(3,4-diethylbenzyl)-N-acetyl-3-(1H-indol-3-yl)-2-[[(4-phenylpiperazin-1-yl)acetyl]amino]propanamide, N-(3,4-dichlorobenzyl)-N-acetyl-3-(1H-indol- 3-yl)-2-[[(4-phenylpiperazin-1-yl)acetyl]amino]propanamide, N-[3,5-bis(trifluoromethyl)benzyl]-N-acetyl-3-(1H-indol-3-yl)-2-[[(4-phenylpiperazin-1-yl)acetyl]amino]propanamide, N-(3,4,5-trimethoxybenzyl)-N-acetyl-3-(1H-indol-3-yl)-2-[[(4-phenylpiperazin-1-yl)acetyl]amino]propanamide, N-(3,4,5-trimethylbenzyl)-N-acetyl-3-(1H-indol-3-yl)-2-[[(4-phenylpiperazin-1-yl)acetyl]amino]propanamide, N-(3,4,5-triethoxybenzyl)-N-acetyl-3-(1H-indol-3-yl)-2-[[(4-phenylpiperazin-1-yl)acetyl]amino]propanamide, N-(3,4,5-triethylbenzyl)-N-acetyl-3-(1H-indol-3-yl)-2-[[(4-phenylpiperazin-1-yl)acetyl]amino]propanamide, N-(3,4,5-trichlorobenzyl)-N-acetyl-3-(1H-indol-3-yl)-2-[[(4-phenylpiperazin-1-yl)acetyl]amino]propanamide, N-[3,4,5-tri(trifluoromethyl)benzyl]-N-acetyl-3-(1H-indol-3-yl)-2-[[(4-phenylpiperazin-1-yl)acetyl]amino]propanamide, N-(2-methoxybenzyl)-N-acetyl-3-(1H-indol-3-yl)-2-[[(4-cyclohexylpiperazin-1-yl)acetyl]amino]propanamide, N-(2-ethoxybenzyl)-N-acetyl-3-(1H-indol-3-yl)-2-[[(4-cyclohexylpiperazin-1-yl)acetyl]amino]propanamide, N-(2-methylbenzyl)-N-acetyl-3-(1H-indol-3-yl)-2-[[(4-cyclohexylpiperazin-1-yl)acetyl]amino]propanamide, N-(2-chlorobenzyl)-N-acetyl-3-(1H-indol-3-yl)-2-[[(4-cyclohexylpiperazin-1-yl)acetyl]amino]propanamide, N-(2-trifluoromethylbenzyl)-N-acetyl-3-(1H-indol-3-yl)-2-[[(4-cyclohexylpiperazin-1-yl)acetyl]amino]propanamide, N-(2-ethylbenzyl)-N-acetyl-3-(1H-indol-3-yl)-2-[[(4-cyclohexylpiperazin-1-yl)acetyl]amino]propanamide, N-(3,4-dimethoxybenzyl)-N-acetyl-3-(1H-indol-3-yl)-2-[[(4-cyclohexylpiperazin-1-yl)acetyl]amino]propanamide, N-(3,4-dimethylbenzyl)-N-acetyl-3-(1H-indol-3-yl)-2-[[(4-cyclohexylpiperazin-1-yl)acetyl]amino]propanamide, N-(3,4-diethoxybenzyl)-N-acetyl-3-(1H-indol-3-yl)-2-[[(4-cyclohexylpiperazin-1-yl)acetyl]amino]propanamide, N-(3,4-diethylbenzyl)-N-acetyl-3-(1H-indol-3-yl)-2-[[(4-cyclohexylpiperazin-1-yl)acetyl]amino]propanamide, N-(3,4-dichlorobenzyl)-N-acetyl-3-(1H-indol-3-yl)-2-[[(4-cyclohexylpiperazin-1-yl)acetyl]amino]propanamide, N-[3,5-bis(trifluoromethyl)benzyl]-N-acetyl-3-(1H-indol-3-yl)-2-[[(4-cyclohexylpiperazin-1-yl)acetyl]amino]propanamide, N-(3,4,5-trimethoxybenzyl)-N-acetyl-3-(1H-indol-3-yl)-2-[[(4-cyclohexylpiperazin-1-yl)acetyl]aminolpropanamide, N-(3,4,5-trimethylbenzyl)-N-acetyl-3-(1H-indol-3-yl)-2-[[(4-cyclohexylpiperazin-1-yl)acetyl]amino]propanamide, N-(3,4,5-triethoxybenzyl)-N-acetyl-3-(1H-indol-3-yl)-2-[[(4-cyclohexylpiperazin- 1-yl)acetyl]aminolpropanamide, N-(3,4,5-triethylbenzyl)-N-acetyl-3-(1H-indol-3-yl)-2-[[(4-cyclohexylpiperazin-1-yl)acetyl]amino]propanamide, N-(3,4,5-trichlorobenzyl)-N-acetyl-3-(1H-indol-3-yl)-2-[[(4-cyclohexylpiperazin-1-yl)acetyl]amino]propanamide, N-[3,4,5-tri(trifluoromethyl)benzyl]-N-acetyl-3-(1H-indol-3-yl)-2-[[(4-cyclohexylpiperazin-1-yl)acetyl]amino]propanamide, N-(2-methoxybenzyl)-N-acetyl-3-(1H-indol-3-yl)-2-[[[4-(piperidin-1-yl)piperidin-1-yl]acetyl]amino]propanamide, N-(2-ethoxybenzyl)-N-acetyl-3-(1H-indol-3-yl)-2-[[[4-(piperidin-1-yl)piperidin-1-yl]acetyl]amino]propanamide, N-(2-methylbenzyl)-N-acetyl-3-(1H-indol-3-yl)-2-[[[4-(piperidin-1-yl)piperidin-1-yl]acetyl]amino]propanamide, N-(2-chlorobenzyl)-N-acetyl-3-(1H-indol-3-yl)-2-[[[4-(piperidin-1-yl)piperidin-1-yl]acetyl]amino]propanamide, N-(2-trifluoromethylbenzyl)-N-acetyl-3-(1H-indol-3-yl)-2-[[[4-(piperidin-1-yl)piperidin-1-yl]acetyl]aminolpropanamide, N-(2-ethylbenzyl)-N-acetyl-3-(1H-indol-3-yl)-2-[[[4-(piperidin-1-yl)piperidin-1-yl]acetyl]amino]propanamide, N-(3,4-dimethoxybenzyl)-N-acetyl-3-(1H-indol-3-yl)-2-[[[4-(piperidin-1-yl)piperidin-1-yl]acetyl]aminolpropanamide, N-(3,4-dimethylbenzyl)-N-acetyl-3-(1H-indol-3-yl)-2-[[[4-(piperidin-1-yl)piperidin-1-yl]acetyl]amino]propanamide, N-(3,4-diethoxybenzyl)-N-acetyl-3-(1H-indol-3-yl)-2-[[[4-(piperidin-1-yl)piperidin-1-yl]acetyl]amino]propanamide, N-(3,4-diethylbenzyl)-N-acetyl-3-(1H-indol-3-yl)-2-[[[4-(piperidin-1-yl)piperidin-1-yl]acetyl]amino]propanamide, N-(3,4-dichlorobenzyl)-N-acetyl-3-(1H-indol-3-yl)-2-[[[4-(piperidin-1-yl)piperidin-1-yl]acetyl]amino]propanamide, N-[3,5-bis(trifluoromethyl)benzyl]-N-acetyl-3-(1H-indol-3-yl)-2-[[[4-(piperidin-1-yl)piperidin-1-yl]acetyl]amino]propanamide, N-(3,4,5-trimethoxybenzyl)-N-acetyl-3-(1H-indol-3-yl)-2-[[[4-(piperidin-1-yl)piperidin-1-yl]acetyl]amino]propanamide, N-(3,4,5-trimethylbenzyl)-N-acetyl-3-(1H-indol-3-yl)-2-[[[4-(piperidin-1-yl)piperidin-1-yl]acetyl]amino]propanamide, N-(3,4,5-triethoxybenzyl)-N-acetyl-3-(1H-indol-3-yl)-2-[[[4-(piperidin-1-yl)piperidin-1-yl]acetyl]amino]propanamide, N-(3,4,5-triethylbenzyl)-N-acetyl-3-(1H-indol-3-yl)-2-[[[4-(piperidin-1-yl)piperidin-1-yl]acetyl]amino]propanamide, N-(3,4,5-trichlorobenzyl)-N-acetyl-3-(1H-indol- 3-yl)-2-[[[4-(piperidin-1-yl)piperidin-1-yl]acetyl]amino]propanamide, N-[3,4,5-tri(trifluoromethyl)benzyl]-N-acetyl-3-(1H-indol-3-yl)-2-[[[4-(piperidin-1-yl)piperidin-1-yl]acetyl]amino]propanamide, N-(2-methoxybenzyl)-3-(1H-indol-3-yl)-2-[[(4-methyl)-2,5-dioxopiperazin-1-yl]acetyl]amino]propanamide, N-(2-ethoxybenzyl)-3-(1H-indol-3-yl)-2-[[(4-methyl)-2,5-dioxopiperazin-1-yl]acetyl]aminolpropanamide, N-(2-methylbenzyl)-3-(1H-indol-3-yl)-2-[[(4-methyl)-2,5-dioxopiperazin-1-yl]acetyl]amino]propanamide, N-(2-chlorobenzyl)-3-(1H-indol-3-yl)-2-[[(4-methyl)-2,5-dioxopiperazin-1-yl]acetyl]amino]propanamide, N-(2-trifluoromethylbenzyl)-3-(1H-indol-3-yl)-2-[[(4-methyl)-2,5-dioxopiperazin-1-yl]acetyl]amino]propanamide, N-(2-ethylbenzyl)-3-(1H-indol-3-yl)-2-[[(4-methyl)-2,5-dioxopiperazin-1-yl]acetyl]amino]propanamide, N-(3,4-dimethoxybenzyl)-3-(1H-indol-3-yl)-2-[[(4-methyl)-2,5-dioxopiperazin-1-yl]acetyl]amino]propanamide, N-(3,4-dimethylbenzyl)-3-(1H-indol-3-yl)-2-[[(4-methyl)-2,5-dioxopiperazin-1-yl]acetyl]amino]propanamide, N-(3,4-diethoxybenzyl)-3-(1H-indol-3-yl)-2-[[(4-methyl)-2,5-dioxopiperazin-1-yl]acetyl]amino]propanamide, N-(3,4-diethylbenzyl)-3-(1H-indol-3-yl)-2-[[(4-methyl)-2,5-dioxopiperazin-1-yl]acetyl]amino]propanamide, N-(3,4-dichlorobenzyl)-3-(1H-indol-3-yl)-2-[[(4-methyl)-2,5-dioxopiperazin-1-yl]acetyl]amino]propanamide, N-[3,5-bis(trifluoromethyl)benzyl]-3-(1H-indol-3-yl)-2-[[(4-methyl)-2,5-dioxopiperazin-1-yl]acetyl]amino]propanamide, N-(3,4,5-trimethoxybenzyl)-3-(1H-indol-3-yl)-2-[[(4-methyl)-2,5-dioxopiperazin-1-yl]acetyl]amino]propanamide, N-(3,4,5-trimethylbenzyl)-3-(1H-indol-3-yl)-2-[[(4-methyl)-2,5-dioxopiperazin-1-yl]acetyl]amino]propanamide, N-(3,4,5-triethoxybenzyl)-3-(1H-indol-3-yl)-2-[[(4-methyl)-2,5-dioxopiperazin-1-yl]acetyl]amino]propanamide, N-(3,4,5- triethylbenzyl)-3-(1H-indol-3-yl)-2-[[(4-methyl)-2,5-dioxopiperazin-1-yl]acetyl]amino]propanamide, N-(3,4,5-trichlorobenzyl)-3-(1H-indol-3-yl)-2-[[(4-methyl)-2,5-dioxopiperazin-1-yl]acetyl]amino]propanamide, and N-[3,4,5-tri(trifluoromethyl)benzyl]-3-(1H-indol-3-yl)-2-[[(4-methyl)-2,5-dioxopiperazin-1-yl]acetyl]amino]propanamide, N-(2-methoxybenzyl)-3-(1H-indol-3-yl)-2-[[(4-cyclohexyl)-2,5-dioxopiperazin-1-yl]acetyl]amino]propanamide, N-(2-ethoxybenzyl)-3-(1H-indol-3-yl)-2-[[(4-cyclohexyl)-2,5-dioxopiperazin-1-yl]acetyl]amino]propanamide, N-(2-methylbenzyl)-3-(1H-indol-3-yl)-2-[[(4-cyclohexyl)-2,5-dioxopiperazin-1-yl]acetyl]amino]propanamide, N-(2-chlorobenzyl)- 3-(1H-indol-3-yl)-2-[[(4-cyclohexyl)-2,5-dioxopiperazin-1-yl]acetyl]amino]propanamide, N-(2-trifluoromethylbenzyl)-3-(1H-indol-3-yl)-2-[[(4-cyclohexyl)-2,5-dioxopiperazin-1-yl]acetyl]amino]propanamide, N-(2-ethylbenzyl)-3-(1H-indol-3-yl)-2-[[(4-cyclohexyl)-2,5-dioxopiperazin-1-yl]acetyl]aminolpropanamide, N-(3,4-dimethoxybenzyl)-3-(1H-indol-3-yl)-2-[[(4-cyclohexyl)-2,5-dioxopiperazin-1-yl]acetyl]amino]propanamide, N-(3,4-dimethylbenzyl)-3-(1H-indol-3-yl)-2-[[(4-cyclohexyl)-2,5-dioxopiperazin-1-yl]acetyl]amino]propanamide, N-(3,4-diethoxybenzyl)-3-(1H-indol-3-yl)-2-[[(4-cyclohexyl)-2,5-dioxopiperazin-1-yl]acetyl]amino]propanamide, N-(3,4-diethylbenzyl)-3-(1H-indol-3-yl)-2-[[(4-cyclohexyl)-2,5-dioxopiperazin-1-yl]acetyl]amino]propanamide, N-(3,4-dichlorobenzyl)-3-(1H-indol-3-yl)-2-[[(4-cyclohexyl)-2,5-dioxopiperazin-1-yl]acetyl]amino]propanamide, N-[3,5-bis(trifluoromethyl)benzyl]-3-(1H-indol-3-yl)-2-[[(4-cyclohexyl)-2,5-dioxopiperazin-1-yl]acetyl]amino]propanamide, N-(3,4,5-trimethoxybenzyl)-3-(1H-indol-3-yl)-2-[[(4-cyclohexyl)-2,5-dioxopiperazin-1-yl]acetyl]amino]propanamide, N-(3,4,5-trimethylbenzyl)-3-(1H-indol-3-yl)-2-[[(4-cyclohexyl)-2,5-dioxopiperazin-1-yl]acetyl]amino]propanamide, N-(3,4,5-triethoxybenzyl)-3-(1H-indol-3-yl)-2-[[(4-cyclohexyl)-2,5-dioxopiperazin-1-yl]acetyl]amino]propanamide, N-(3,4,5-triethylbenzyl)-3-(1H-indol-3-yl)-2-[[(4-cyclohexyl)-2,5-dioxopiperazin-1-yl]acetyl]amino]propanamide, N-(3,4,5-trichlorobenzyl)-3-(1H-indol-3-yl)-2-[[(4-cyclohexyl)-2,5-dioxopiperazin-1-yl]acetyl]amino]propanamide, and N-[3,4,5-tri(trifluoromethyl)benzyl]-3-(1H-indol-3-yl)-2-[[(4-cyclohexyl)-2,5-dioxopiperazin-1-yl]acetyl]amino]propanamide, N-(2-methoxybenzyl)-3-(1H-indol-3-yl)-2-[[(4-benzyl)-2,5-dioxopiperazin-1-yl]acetyl]amino]propanamide, N-(2-ethoxybenzyl)-3-(1H-indol-3-yl)-2-[[(4-benzyl)-2,5-dioxopiperazin-1-yl]acetyl]amino]propanamide, N-(2-methylbenzyl)-3-(1H-indol-3-yl)-2-[[(4-benzyl)-2,5-dioxopiperazin-1-yl]acetyl]amino]propanamide, N-(2-chlorobenzyl)-3-(1H-indol-3-yl)-2-[[(4-benzyl)-2,5-dioxopiperazin-1-yl]acetyl]amino]propanamide, N-(2-trifluoromethylbenzyl)-3-(1H-indol-3-yl)-2-[[(4-benzyl)-2,5-dioxopiperazin-1-yl]acetyl]amino]propanamide, N-(2-ethylbenzyl)-3-(1H-indol-3-yl)-2-[[(4-benzyl)-2,5-dioxopiperazin-1-yl]acetyl]amino]propanamide, N-(3,4-dimethoxybenzyl)-3-(1H-indol-3-yl)-2-[[(4-benzyl)-2,5-dioxopiperazin-1-yl]acetyl]amino]propanamide, N-(3,4-dimethylbenzyl)-3-(1H-indol-3-yl)-2-[[(4-benzyl)-2,5-dioxopiperazin-1-yl]acetyl]amino]propanamide, N-(3,4-diethoxybenzyl)-3-(1H-indol-3-yl)-2-[[(4-benzyl)-2,5-dioxopiperazin-1-yl]acetyl]amino]propanamide, N-(3,4-diethylbenzyl)-3-(1H-indol-3-yl)-2-[[(4-benzyl)-2,5-dioxopiperazin-1-yl]acetyl]amino]propanamide, N-(3,4-dichlorobenzyl)-3-(1H-indol-3-yl)-2-[[(4-benzyl)-2,5-dioxopiperazin-1-yl]acetyl]amino]propanamide, N-[3,5-bis(trifluoromethyl)benzyl]-3-(1H-indol-3-yl)-2-[[(4-benzyl)-2,5-dioxopiperazin-1-yl]acetyl]amino]propanamide, N-(3,4,5-trimethoxybenzyl)-3-(1H-indol-3-yl)-2-[[(4-benzyl)-2,5-dioxopiperazin-1-yl]acetyl]amino]propanamide, N-(3,4,5-trimethylbenzyl)-3-(1H-indol-3-yl)-2-[[(4-benzyl)-2,5-dioxopiperazin-1-yl]acetyl]amino]propanamide, N-(3,4,5-triethoxybenzyl)-3-(1H-indol-3-yl)-2-[[(4-benzyl)-2,5-dioxopiperazin-1-yl]acetyl]amino]propanamide, N-(3,4,5-triethylbenzyl)-3-(1H-indol-3-yl)-2-[[(4-benzyl)-2,5-dioxopiperazin-1-yl]acetyl]amino]propanamide, N-(3,4,5-trichlorobenzyl)-3-(1H-indol-3-yl)-2-[[(4-benzyl)-2,5-dioxopiperazin-1-yl]acetyl]amino]propanamide, and N-[3,4,5-tri(trifluoromethyl)benzyl]-3-(1H-indol-3-yl)-2-[[(4-benzyl)-2,5-dioxopiperazin-1-yl]acetyl]amino]propanamide, N-(2-methoxybenzyl)-3-(1H-indol-3-yl)-2-[[(4-phenyl)-2,5-dioxopiperazin-1-yl]acetyl]amino]propanamide, N-(2-ethoxybenzyl)-3-(1H-indol-3-yl)-2-[[(4-phenyl)-2,5-dioxopiperazin-1-yl]acetyl]amino]propanamide, N-(2-methylbenzyl)-3-(1H-indol-3-yl)-2-[[(4-phenyl)-2,5-dioxopiperazin-1-yl]acetyl]amino]propanamide, N-(2-chlorobenzyl)-3-(1H-indol-3-yl)-2-[[(4-phenyl)-2,5-dioxopiperazin-1-yl]acetyl]amino]propanamide, N-(2-trifluoromethylbenzyl)-3-(1H-indol-3-yl)-2-[[(4-phenyl)-2,5-dioxopiperazin-1-yl]acetyl]amino]propanamide, N-(2-ethylbenzyl)-3-(1H-indol-3-yl)-2-[[(4-phenyl)-2,5-dioxopiperazin-1-yl]acetyl]amino]propanamide, N-(3,4-dimethoxybenzyl)-3-(1H-indol-3-yl)-2-[[(4-phenyl)-2,5-dioxopiperazin-1-yl]acetyl]amino]propanamide, N-(3,4-dimethylbenzyl)-3-(1H-indol-3-yl)-2-[[(4-phenyl)-2,5-dioxopiperazin-1-yl]acetyl]amino]propanamide, N-(3,4-diethoxybenzyl)-3-(1H-indol-3-yl)-2-[[(4-phenyl)-2,5-dioxopiperazin-1-yl]acetyl]amino]propanamide, N-(3,4-diethylbenzyl)-3-(1H-indol-3-yl)-2-[[(4-phenyl)-2,5-dioxopiperazin-1-yl]acetyl]amino]propanamide, N-(3,4-dichlorobenzyl)-3-(1H-indol-3-yl)-2-[[(4-phenyl)-2,5-dioxopiperazin-1-yl]acetyl]amino]propanamide, N-[3,5-bis(trifluoromethyl)benzyl]-3-(1H-indol-3-yl)-2-[[(4-phenyl)-2,5-dioxopiperazin-1-yl]acetyl]amino]propanamide, N-(3,4,5-trimethoxybenzyl)- 3-(1H-indol-3-yl)-2-[[(4-phenyl)-2,5-dioxopiperazin-1-yl]acetyl]amino]propanamide, N-(3,4,5-trimethylbenzyl)-3-(1H-indol-3-yl)-2-[[(4-phenyl)-2,5-dioxopiperazin-1-yl]acetyl]amino]propanamide, N-(3,4,5-triethoxybenzyl)-3-(1H-indol-3-yl)-2-[[(4-phenyl)-2,5-dioxopiperazin-1-yl]acetyl]amino]propanamide, N-(3,4,5-triethylbenzyl)-3-(1H-indol-3-yl)-2-[[(4-phenyl)-2,5-dioxopiperazin-1-yl]acetyl]amino]propanamide, N-(3,4,5-trichlorobenzyl)-3-(1H-indol-3-yl)-2-[[(4-phenyl)-2,5-dioxopiperazin-1-yl]acetyl]amino]propanamide, and N-[3,4,5-tri(trifluoromethyl)benzyl]-3-(1H-indol-3-yl)-2-[[(4-phenyl)-2,5-dioxopiperazin-1-yl]acetyl]amino]propanamide, N-(2-methoxybenzyl)-N-methyl-3-(1H-indol-3-yl)-2-[[(4-phenylpiperazin-1-yl)acetyl]amino]propanamide, N-(2-ethoxybenzyl)-N-methyl-3-(1H-indol-3-yl)-2-[[(4-phenylpiperazin-1-yl)acetyl]amino]propanamide, N-(2-methylbenzyl)-N-methyl-3-(1H-indol-3-yl)-2-[[(4-phenylpiperazin-1-yl)acetyl]amino]propanamide, N-(2-chlorobenzyl)-N-methyl-3-(1H-indol-3-yl)-2-[[(4-phenylpiperazin-1-yl)acetyl]amino]propanamide, N-(2-trifluoromethylbenzyl)-N-methyl-3-(1H-indol-3-yl)-2-[[(4-phenylpiperazin-1-yl)acetyl]amino]propanamide, N-(2-ethylbenzyl)-N-methyl-3-(1H-indol-3-yl)-2-[[(4-phenylpiperazin-1-yl)acetyl]amino]propanamide, N-(3,4-dimethoxybenzyl)-N-methyl-3-(1H-indol-3-yl)-2-[[(4-phenylpiperazin-1-yl)acetyl]amino]propanamide, N-(3,4-dimethylbenzyl)-N-methyl-3-(1H-indol-3-yl)-2-[[(4-phenylpiperazin-1-yl)acetyl]amino]propanamide, N-(3,4-diethoxybenzyl)-N-methyl-3-(1H-indol-3-yl)-2-[[(4-phenylpiperazin-1-yl)acetyl]amino]propanamide, N-(3,4-diethylbenzyl)-N-methyl-3-(1H-indol-3-yl)-2-[[(4- phenylpiperazin-1-yl)acetyl]amino]propanamide, N-(3,4-dichlorobenzyl)-N-methyl-3-(1H-indol-3-yl)-2-[[(4-phenylpiperazin-1-yl)acetyl]amino]propanamide, N-[3,5-bis(trifluoromethyl)benzyl]-N-methyl-3-(1H-indol-3-yl)-2-[[(4-phenylpiperazin-1-yl)acetyl]amino]propanamide, N-(3,4,5-trimethoxybenzyl)-N-methyl-3-(1H-indol-3-yl)-2-[[(4-phenylpiperazin-1-yl)acetyl]amino]propanamide, N-(3,4,5-trimethylbenzyl)-N-methyl-3-(1H-indol-3-yl)-2-[[(4-phenylpiperazin-1-yl)acetyl]amino]propanamide, N-(3,4,5-triethoxybenzyl)-N-methyl-3-(1H-indol-3-yl)-2-[[(4-phenylpiperazin-1-yl)acetyl]amino]propanamide, N-(3,4,5-triethylbenzyl)-N-methyl-3-(1H-indol-3-yl)-2-[[(4-phenylpiperazin-1-yl)acetyl]amino]propanamide, N-(3,4,5-trichlorobenzyl)-N-methyl-3-(1H-indol-3-yl)-2-[[(4-phenylpiperazin-1-yl)acetyl]amino]propanamide, N-[3,4,5-tri(trifluoromethyl)benzyl]-N-methyl- 3-(1H-indol-3-yl)-2-[[(4-phenylpiperazin-1-yl)acetyl]amino]propanamide, N-(2-methoxybenzyl)-N-methyl-3-(1H-indol-3-yl)-2-[[(4-cyclohexylpiperazin-1-yl)acetyl]amino]propanamide, N-(2-ethoxybenzyl)-N-methyl-3-(1H-indol-3-yl)-2-[[(4-cyclohexylpiperazin-1-yl)acetyl]amino]propanamide, N-(2-methylbenzyl)-N-methyl-3-(1H-indol-3-yl)-2-[[(4-cyclohexylpiperazin-1-yl)acetyl]aminolpropanamide, N-(2-chlorobenzyl)-N-methyl-3-(1H-indol-3-yl)-2-[[(4-cyclohexylpiperazin-1-yl)acetyl]amino]propanamide, N-(2-trifluoromethylbenzyl)-N-methyl-3-(1H-indol-3-yl)-2-[[(4-cyclohexylpiperazin-1-yl)acetyl]aminolpropanamide, N-(2-ethylbenzyl)-N-methyl-3-(1H-indol-3-yl)-2-[[(4-cyclohexylpiperazin-1-yl)acetyl]amino]propanamide, N-(3,4-dimethoxybenzyl)-N-methyl-3-(1H-indol-3-yl)-2-[[(4-cyclohexylpiperazin-1-yl)acetyl]amino]propanamide, N-(3,4-dimethylbenzyl)-N-methyl-3-(1H-indol-3-yl)-2-[[(4-cyclohexylpiperazin-1-yl)acetyl]amino]propanamide, N-(3,4-diethoxybenzyl)-N-methyl-3-(1H-indol-3-yl)-2-[[(4-cyclohexylpiperazin-1-yl)acetyl]amino]propanamide, N-(3,4-diethylbenzyl)-N-methyl-3-(1H-indol-3-yl)-2-[[(4-cyclohexylpiperazin-1-yl)acetyl]amino]propanamide, N-(3,4-dichlorobenzyl)-N-methyl-3-(1H-indol-3-yl)-2-[[(4-cyclohexylpiperazin-1-yl)acetyl]amino]propanamide, N-[3,5-bis(trifluoromethyl)benzyl]-N-methyl-3-(1H-indol-3-yl)-2-[[(4-cyclohexylpiperazin-1-yl)acetyl]amino]propanamide, N-(3,4,5-trimethoxybenzyl)-N-methyl-3-(1H-indol-3-yl)-2-[[(4-cyclohexylpiperazin-1-yl)acetyl]amino]propanamide, N-(3,4,5-trimethylbenzyl)-N-methyl-3-(1H-indol-3-yl)-2-[[(4-cyclohexylpiperazin-1-yl)acetyl]amino]propanamide, N-(3,4,5-triethoxybenzyl)-N-methyl-3-(1H-indol-3-yl)-2-[[(4-cyclohexylpiperazin-1-yl)acetyl]amino]propanamide, N-(3,4,5-triethylbenzyl)-N-methyl-3-(1H-indol-3-yl)-2-[[(4-cyclohexylpiperazin-1-yl)acetyl]amino]propanamide, N-(3,4,5-trichlorobenzyl)-N-methyl-3-(1H-indol-3-yl)-2-[[(4-cyclohexylpiperazin-1-yl)acetyl]amino]propanamide, N-[3,4,5-tri(trifluoromethyl)benzyl]-N-methyl-3-(1H-indol-3-yl)-2-[[(4-cyclohexylpiperazin-1-yl)acetyl]amino]propanamide, N-(2-methoxybenzyl)-N-methyl-3-(1H-indol-3-yl)-2-[[[4-(piperidin-1-yl)piperidin-1-yl]acetyl]amino]propanamide, N-(2-ethoxybenzyl)-N-methyl-3-(1H-indol-3-yl)-2-[[[4-(piperidin-1-yl)piperidin-1-yl]acetyl]amino]propanamide, N-(2-methylbenzyl)-N-methyl-3-(1H-indol-3-yl)-2-[[[4-(piperidin-1-yl)piperidin-1-yl]acetyl]amino]propanamide, N-(2-chlorobenzyl)-N-methyl-3-(1H-indol-3-yl)-2-[[[4-(piperidin-1-yl)piperidin-1-yl]acetyl]amino]propanamide, N-(2-trifluoromethylbenzyl)-N-methyl-3-(1H-indol-3-yl)-2-[[[4-(piperidin-1-yl)piperidin-1-yl]acetyl]amino]propanamide, N-(2-ethylbenzyl)-N-methyl-3-(1H-indol-3-yl)-2-[[[4-(piperidin-1-yl)piperidin-1-yl]acetyl]amino]propanamide, N-(3,4-dimethoxybenzyl)-N-methyl-3-(1H-indol-3-yl)-2-[[[4-(piperidin-1-yl)piperidin-1-yl]acetyl]amino]propanamide, N-(3,4-dimethylbenzyl)-N-methyl-3-(1H-indol-3-yl)-2-[[[4-(piperidin-1-yl)piperidin-1-yl]acetyl]amino]propanamide, N-(3,4-diethoxybenzyl)-N-methyl-3-(1H-indol-3-yl)-2-[[[4-(piperidin-1-yl)piperidin-1-yl]acetyl]aminolpropanamide, N-(3,4-diethylbenzyl)-N-methyl-3-(1H-indol-3-yl)-2-[[[4-(piperidin-1-yl)piperidin-1-yl]acetyl]amino]propanamide, N-(3,4-dichlorobenzyl)-N-methyl-3-(1H-indol-3-yl)-2-[[[4-(piperidin-1-yl)piperidin-1-yl]acetyl]amino]propanamide, N-[3,5-bis(trifluoromethyl)benzyl]-N-methyl-3-(1H-indol-3-yl)-2-[[[4-(piperidin-1-yl)piperidin-1-yl]acetyl]amino]propanamide, N-(3,4,5-trimethoxybenzyl)-N-methyl-3-(1H-indol-3-yl )-2-[[[4-(piperidin-1-yl)piperidin-1-yl]acetyl]amino]propanamide, N-(3,4,5-trimethylbenzyl)-N-methyl-3-(1H-indol-3-yl)-2-[[[4-(piperidin-1-yl)piperidin-1-yl]acetyl]amino]propanamide, N-(3,4,5-triethoxybenzyl)-N-methyl-3-(1H-indol-3-yl)-2-[[[4-(piperidin-1-yl)piperidin-1-yl]acetyl]amino]propanamide, N-(3,4,5-triethylbenzyl)-N-methyl-3-(1H-indol-3-yl)-2-[[[4-(piperidin-1-yl)piperidin-1-yl]acetyl]amino]propanamide, N-(3,4,5-trichlorobenzyl)-N-methyl-3-(1H-indol-3-yl)-2-[[[4-(piperidin-1-yl)piperidin-1-yl]acetyl]amino]propanamide, N-[3,4,5-tri(trifluoromethyl)benzyl]-N-methyl-3-(1H-indol-3-yl)-2-[[[4-(piperidin-1-yl)piperidin-1-yl]acetyl]amino]propanamide, N-methyl-N-(2-methoxybenzyl)-3-(1H-indol-3-yl)-2-[[(4-methyl)-2,5-dioxopiperazin-1-yl]acetyl]amino]propanamide, N-methyl-N-(2-ethoxybenzyl)-3-(1H-indol-3-yl)-2-[[(4-methyl)-2,5-dioxopiperazin-1-yl]acetyl]amino]propanamide, N-methyl-N-(2-methylbenzyl)-3-(1H-indol-3-yl)-2-[[(4-methyl)-2,5-dioxopiperazin-1-yl]acetyl]amino]propanamide, N-methyl-N-(2-chlorobenzyl)-3-(1H-indol-3-yl)-2-[[(4-methyl)-2,5-dioxopiperazin-1-yl]acetyl]amino]propanamide, N-methyl-N-(2-trifluoromethylbenzyl)-3-(1H-indol-3-yl)-2-[[(4-methyl)-2,5-dioxopiperazin-1-yl]acetyl]amino]propanamide, N-methyl-N-(2-ethylbenzyl)-3-(1H-indol-3-yl)-2-[[(4-methyl)-2,5-dioxopiperazin-1-yl]acetyl]amino]propanamide, N-methyl-N-(3,4-dimethoxybenzyl)-3-(1H-indol-3-yl)-2-[[(4-methyl)-2,5-dioxopiperazin-1-yl]acetyl]amino]propanamide, N-methyl-N-(3,4-dimethylbenzyl)-3-(1H-indol-3-yl)-2-[[(4-methyl)-2,5-dioxopiperazin-1-yl]acetyl]amino]propanamide, N-methyl-N-(3,4-diethoxybenzyl)-3-(1H-indol-3-yl)-2-[[(4-methyl)-2,5-dioxopiperazin-1-yl]acetyl]amino]propanamide, N-methyl-N-(3,4-diethylbenzyl)-3-(1H-indol-3-yl)-2-[[[(4-methyl)-2,5-dioxopiperazin-1-yl]acetyl]amino]propanamide, N-methyl-N-(3,4-dichlorobenzyl)-3-(1H-indol-3-yl)-2-[[(4-methyl)-2,5-dioxopiperazin-1-yl]acetyl]amino]propanamide, N-[3,5-bis(trifluoromethyl)benzyl]-3-(1H-indol-3-yl)-2-[[(4-methyl)-2,5-dioxopiperazin-1-yl]acetyl]amino]propanamide, N-methyl-N-(3,4,5-trimethoxybenzyl)-3-(1H-indol-3-yl)-2-[[(4-methyl)-2,5-dioxopiperazin-1-yl]acetyl]amino]propanamide, N-methyl-N-(3,4,5-trimethylbenzyl)-3-(1H-indol-3-yl)-2-[[(4-methyl)-2,5-dioxopiperazin-1-yl]acetyl]amino]propanamide, N-methyl-N-(3,4,5-triethoxybenzyl)-3-(1H-indol-3-yl)-2-[[(4-methyl)-2,5-dioxopiperazin 1-yl]acetyl]amino]propanamide, N-methyl-N-(3,4,5-triethylbenzyl)-3-(1H-indol-3-yl)-2-[[(4-methyl)-2,5-dioxopiperazin 1-yl]acetyl]amino]propanamide, N-methyl-N-(3,4,5-trichlorobenzyl)-3-(1H-indol-3-yl)-2-[[(4-methyl)-2,5-dioxopiperazin-1-yl]acetyl]amino]propanamide, and N-[3,4,5-tri(trifluoromethyl)benzyl]-3-(1H-indol-3-yl)-2-[[(4-methyl)-2,5-dioxopiperazin-1-yl]acetyl]amino]propanamide, N-methyl-N-(2-methoxybenzyl)-3-(1H-indol-3-yl)-2-[[(4-cyclohexyl)-2,5-dioxopiperazin 1-yl]acetyl]amino]propanamide, N-methy-N-(2-ethoxybenzyl)-3-(1H- indol-3-yl)-2-[[(4-cyclohexyl)-2,5-dioxopiperazin-1-yl]acetyl]amino]propanamide, N-methyl-N-(2-methylbenzyl)-3-(1H-indol-3-yl)-2-[[(4-cyclohexyl)-2,5-dioxopiperazin-1-yl]acetyl]amino]propanamide, N-methyl-N-(2-chlorobenzyl)-3-(1H-indol-3-yl)-2-[[(4-cyclohexyl)-2,5-dioxopiperazin-1-yl]acetyl]amino]propanamide, N-methyl-N-(2-trifluoromethylbenzyl)-3-( 1H-indol-3-yl)-2-[[(4-cyclohexyl)-2,5-dioxopiperazin-1-yl]acetyl]amino]propanamide, N-methyl-N-(2-ethylbenzyl)-3-(1H-indol-3-yl)-2-[[(4-cyclohexyl)-2,5-dioxopiperazin-1-yl]acetyl]amino]propanamide, N-methyl-N-(3,4-dimethoxybenzyl)-3-(1H-indol-3-yl)-2-[[(4-cyclohexyl)-2,5-dioxopiperazin-1-yl]acetyl]amino]propanamide, N-methyl-N-(3,4-dimethylbenzyl)-3-(1H-indol-3-yl)-2-[[(4-cyclohexyl)-2,5-dioxopiperazin-1-yl]acetyl]amino]propanamide, N-methyl-N-(3,4-diethoxybenzyl)-3-(1H-indol-3-yl)-2-[[(4-cyclohexyl)-2,5-dioxopiperazin-1-yl]acetyl]amino]propanamide, N-methyl-N-(3,4-diethylbenzyl)-3-(1H-indol-3-yl)-2-[[(4-cyclohexyl)-2,5-dioxopiperazin-1-yl]acetyl]amino]propanamide, N-methyl-N-(3,4-dichlorobenzyl)-3-(1H-indol-3-yl)-2-[[(4-cyclohexyl)-2,5-dioxopiperazin-1-yl]acetyl]amino]propanamide, N-[3,5-bis(trifluoromethyl)benzyl]-3-(1H-indol-3-yl)-2-[[(4-cyclohexyl)-2,5-dioxopiperazin-1-yl]acetyl]amino]propanamide, N-methyl-N-(3,4,5-trimethoxybenzyl)-3-(1H-indol-3-yl)-2-[[(4-cyclohexyl)-2,5-dioxopiperazin-1-yl]acetyl]amino]propanamide, N-methyl-N-(3,4,5-trimethylbenzyl)-3-(1H-indol-3-yl)-2-[[(4-cyclohexyl)-2,5-dioxopiperazin-1-yl]acetyl]amino]propanamide, N-methyl-N-(3,4,5-triethoxybenzyl)-3-(1H-indol-3-yl)-2-[[(4-cyclohexyl)-2,5-dioxopiperazin-1-yl]acetyl]amino]propanamide, N-methyl-N-(3,4,5-triethylbenzyl)-3-(1H-indol-3-yl)-2-[[(4-cyclohexyl)-2,5-dioxopiperazin-1-yl]acetyl]amino]propanamide, N-methyl-N-(3,4,5-trichlorobenzyl)-3-(1H-indol-3-yl)-2-[[(4-cyclohexyl)-2,5-dioxopiperazin-1-yl]acetyl]amino]propanamide, and N-[3,4,5-tri(trifluoromethyl)benzyl]-3-(1H-indol-3-yl)-2-[[(4-cyclohexyl)-2,5-dioxopiperazin-1-yl]acetyl]amino]propanamide, N-methyl-N-(2-methoxybenzyl)-3-(1H-indol-3-yl)-2-[[(4-benzyl)-2,5-dioxopiperazin-1-yl]acetyl]amino]propanamide, N-methyl-N-(2-ethoxybenzyl)-3-(1H-indol-3-yl)-2-[[(4-benzyl)-2,5-dioxopiperazin-1-yl]acetyl]amino]propanamide, N-methyl-N-(2-methylbenzyl)-3-(1H-indol-3-yl)-2-[[(4-benzyl)-2,5-dioxopiperazin-1-yl]acetyl]amino]propanamide, N-methyl-N-(2-chlorobenzyl)-3-(1H-indol-3-yl)- 2-[[(4-benzyl)-2,5-dioxopiperazin-1-yl]acetyl]amino]propanamide, N-methyl-N-(2-trifluoromethylbenzyl)-3-(1H-indol-3-yl)-2-[[(4-benzyl)-2,5-dioxopiperazin-1-yl]acetyl]amino]propanamide, N-methyl-N-(2-ethylbenzyl)-3-(1H-indol-3-yl)- 2-[[(4-benzyl)-2,5-dioxopiperazin-1-yl]acetyl]amino]propanamide, N-methyl-N-(3,4-dimethoxybenzyl)-3-(1H-indol-3-yl)-2-[[(4-benzyl)-2,5-dioxopiperazin-1-yl]acetyl]amino]propanamide, N-methyl-N-(3,4-dimethylbenzyl)-3-(1H-indol-3-yl)-2-[[(4-benzyl)-2,5-dioxopiperazin-1-yl]acetyl]amino]propanamide, N-methyl-N-(3,4-diethoxybenzyl)-3-(1H-indol-3-yl)-2-[[(4-benzyl)-2,5-dioxopiperazin-1-yl]acetyl]amino]propanamide, N-methyl-N-(3,4-diethylbenzyl)-3-(1H-indol-3-yl)-2-[[(4-benzyl)-2,5-dioxopiperazin-1-yl]acetyl]amino]propanamide, N-methyl-N-(3,4-dichlorobenzyl)-3-(1H-indol-3-yl)-2-[[(4-benzyl)-2,5-dioxopiperazin-1-yl]acetyl]amino]propanamide, N-[3,5-bis(trifluoromethyl)benzyl]-3-(1H-indol-3-yl)-2-[[(4-benzyl)-2,5-dioxopiperazin-1-yl]acetyl]amino]propanamide, N-methyl-N-(3,4,5-trimethoxybenzyl)-3-(1H-indol-3-yl)-2-[[(4-benzyl)-2,5-dioxopiperazin-1-yl]acetyl]amino]propanamide, N-methyl-N-(3,4,5-trimethylbenzyl)-3-(1H-indol-3-yl)-2-[[(4-benzyl)-2,5-dioxopiperazin-1-yl]acetyl]amino]propanamide, N-methyl-N-(3,4,5-triethoxybenzyl)-3-(1H-indol-3-yl)-2-[[(4-benzyl)-2,5-dioxopiperazin-1-yl]acetyl]amino]propanamide, N-methyl-N-(3,4,5-triethylbenzyl)-3-(1H-indol-3-yl)-2-[[(4-benzyl)-2,5-dioxopiperazin-1-yl]acetyl]amino]propanamide, N-methyl-N-(3,4,5-trichlorobenzyl)-3-(1H-indol-3-yl)-2-[[(4-benzyl)-2,5-dioxopiperazin-1-yl]acetyl]amino]propanamide, and N-[3,4,5-tri(trifluoromethyl)benzyl]-3-(1H-indol-3-yl)-2-[[(4-benzyl)-2,5-dioxopiperazin 1-yl]acetyl]amino]propanamide, N-methyl-N-(2-methoxybenzyl)-3-(1H-indol-3-yl)-2-[[(4-phenyl)-2,5-dioxopiperazin-1-yl]acetyl]amino]propanamide, N-methyl-N-(2-ethoxybenzyl)-3-(1H-indol-3-yl)-2-[[(4-phenyl)-2,5-dioxopiperazin-1-yl]acetyl]amino]propanamide, N-methyl-N-(2-methylbenzyl)-3-(1H-indol-3-yl)-2-[[(4-phenyl)-2,5-dioxopiperazin-1-yl]acetyl]amino]propanamide, N-methyl-N-(2-chlorobenzyl)-3-(1H-indol-3-yl)-2-[[(4-phenyl)-2,5-dioxopiperazin-1-yl]acetyl]amino]propanamide, N-methyl-N-(2-trifluoromethylbenzyl)-3-(1H-indol-3-yl)-2-[[(4-phenyl)-2,5-dioxopiperazin-1-yl]acetyl]amino]propanamide, N-methyl-N-(2-ethylbenzyl)-3-(1H-indol-3-yl)-2-[[(4-phenyl)-2,5-dioxopiperazin-1-yl]acetyl]amino]propanamide, N-methyl-N-(3,4-dimethoxybenzyl)-3-(1H-indol-3-yl)-2-[[(4-phenyl)-2,5-dioxopiperazin- 1-yl]acetyl]amino]propanamide, N-methyl-N-(3,4-dimethylbenzyl)-3-(1H-indol-3-yl)-2-[[(4-phenyl)-2,5-dioxopiperazin-1-yl]acetyl]amino]propanamide, N-methyl-N-(3,4-diethoxybenzyl)-3-(1H-indol-3-yl)-2-[[(4-phenyl)-2,5-dioxopiperazin-1-yl]acetyl]amino]propanamide, N-methyl-N-(3,4-diethylbenzyl)-3-(1H-indol-3-yl)-2-[[(4-phenyl)-2,5-dioxopiperazin-1-yl]acetyl]amino]propanamide, N-methyl-N-(3,4-dichlorobenzyl)-3-(1H-indol-3-yl)-2-[[(4-phenyl)-2,5-dioxopiperazin-1-yl]acetyl]amino]propanamide, N-[3,5-bis(trifluoromethyl)benzyl]-3-(1H-indol-3-yl)-2-[[(4-phenyl)-2,5-dioxopiperazin-1-yl]acetyl]amino]propanamide, N-methyl-N-(3,4,5-trimethoxybenzyl)-3-(1H-indol-3-yl)-2-[[(4-phenyl)-2,5-dioxopiperazin-1-yl]acetyl]amino]propanamide, N-methyl-N-(3,4,5-trimethylbenzyl)-3-(1H-indol-3-yl)-2-[[(4-phenyl)-2,5-dioxopiperazin-1-yl]acetyl]amino]propanamide, N-methyl-N-(3,4,5-triethoxybenzyl)-3-(1H-indol-3-yl)-2-[[(4-phenyl)-2,5-dioxopiperazin-1-yl]acetyl]amino]propanamide, N-methyl-N-(3,4,5-triethylbenzyl)-3-(1H-indol-3-yl)-2-[[(4-phenyl)-2,5-dioxopiperazin-1-yl]acetyl]amino]propanamide, N-methyl-N-(3,4,5-trichlorobenzyl)-3-(1H-indol-3-yl)-2-[[(4-phenyl)-2,5-dioxopiperazin-1-yl]acetyl]amino]propanamide, and N-[3,4,5-tri(trifluoromethyl)benzyl]-3-(1H-indol-3-yl)-2-[[(4-phenyl)-2,5-dioxopiperazin-1-yl]acetyl]amino]propanamide, and the salts, solvates, and prodrugs thereof.

A preferred process for preparing the compounds of Formula I is by the acylation of the primary amine of a compound of Formula II

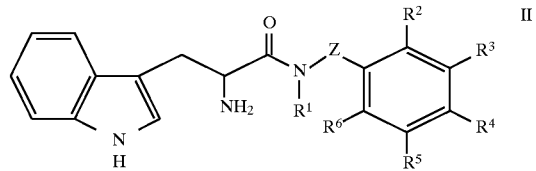

or a salt or solvate thereof.

The acylation of this primary amine can be accomplished by a number of methods known in the art. One such reaction scheme is a substitution using an anhydride such as acetic anhydride or another activated carboxylate, such as a carboxylic acid halide.

Another preferred reaction scheme often employed to acylate a primary amine employs a carboxylic acid of Formula III

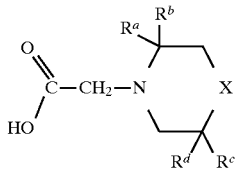

or a salt or solvate thereof, preferably with an activating agent, such as 1,1-carbonyldiimidazole, dicyclohexylcarbodiimide, diethyl azodicarboxylate, 1-hydroxybenzotriazole, alkyl chloroformate and triethylamine, phenyldichlorophosphate, and chlorosulfonyl isocyanate.

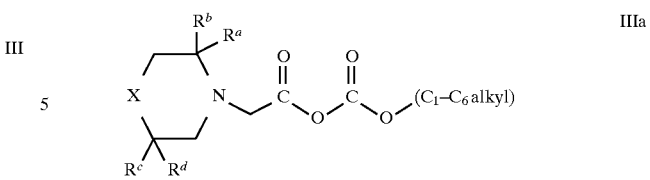

This intermediate is then reacted with a compound of Formula II, or a salt thereof, optionally in the presence of a base.

The intermediates of Formula II are generally prepared using techniques which are well known to those of skill in the art. See., e.g., Patent Cooperation Treaty published application WO 93/01169, published Jan. 21, 1993. Once such synthesis scheme using standard techniques is depicted in Scheme I, infra.

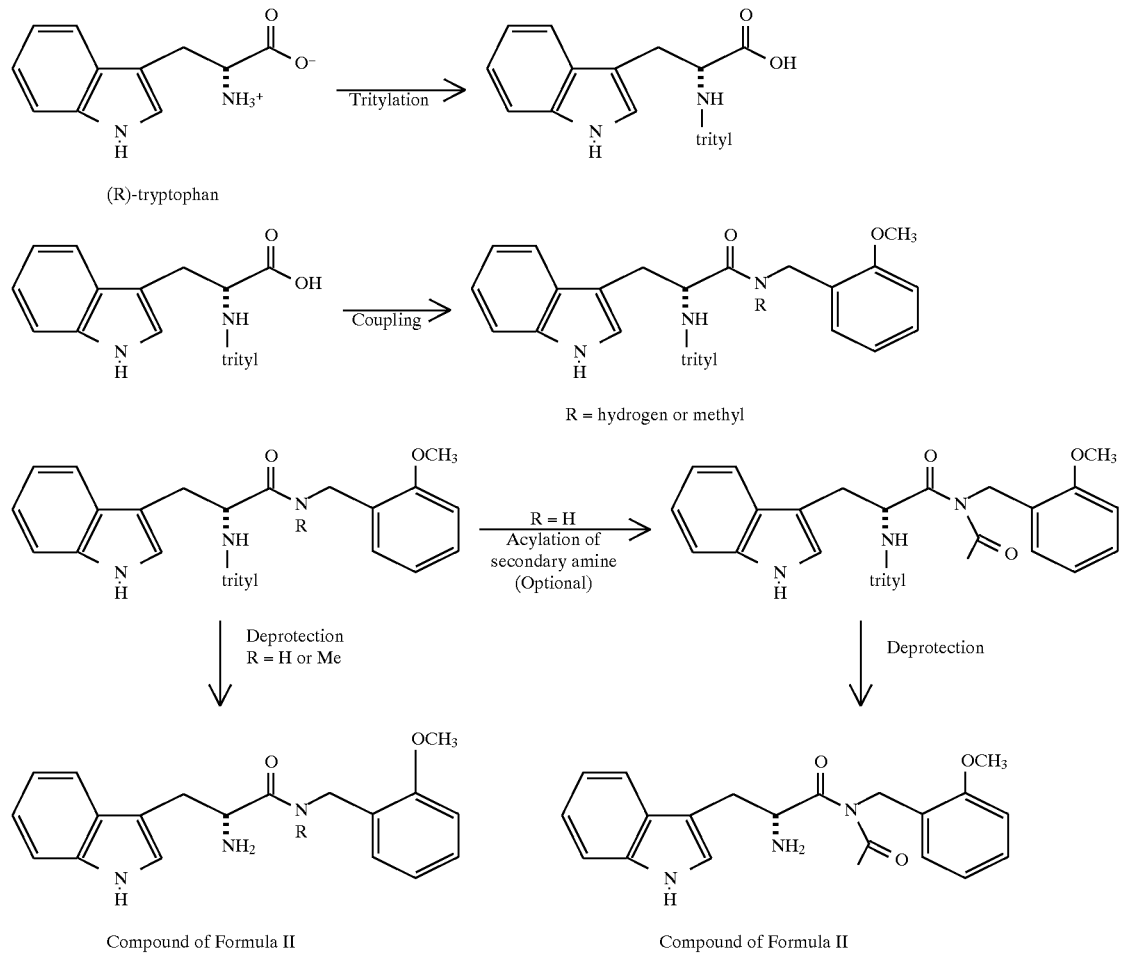

An amino-de-alkoxylation type of reaction uses esters as a means of acylating the primary amine. Activated esters which are attenuated to provide enhanced selectivity are very efficient acylating agents.

In an especially preferred embodiment, a compound of Formula III, or a salt thereof, is first reacted with a suitable haloformate, forming the mixed anhydride of Formula IIIa.

In an alternative embodiment the compounds of Formula I may be prepared from intermediates of Formula IV

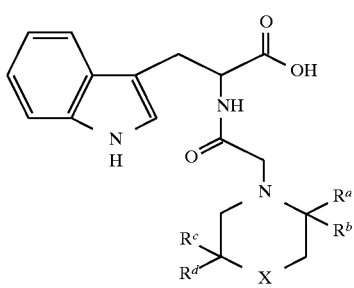

by reaction with compounds of Formula IVa.

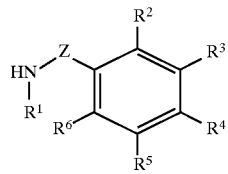

This reaction is preferably performed in the presence of a coupling agent, such as dicyclohexylcarbodiimide.

Intermediates of Formula IV are commercially available or may be prepared by standard syntheses of amino acids. Such syntheses are well known to persons of ordinary skill in the art and are described, for example, in CHEMISTRY AND BIOCHEMISTRY OF AMINO ACIDS, (G. C. Chapman ed., 1985).

During any of the above synthetic sequences it may be necessary or desirable to protect sensitive or reactive groups on any of the molecules concerned. This may be achieved by conventional protecting groups as described supra.

The following Examples and Preparations are illustrative of the processes employed in the synthesis of the compounds of the present invention. As would be understood by persons skilled in the art, other synthetic schemes may be employed to prepare the compounds of the instant invention.

PREPARATION 1

Preparation of 2-t-butoxycarbonylamino-3-(1H-indol-3-yl)-N-(2-methoxybenzyl)propanamide

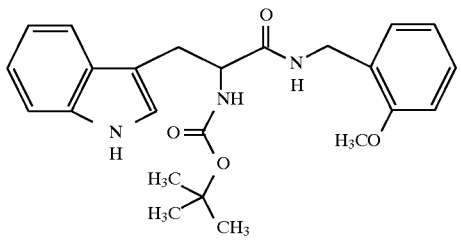

To a solution of N-(t-butoxycarbonyl)tryptophan (46.4 g, 152.6 mmol) in 500 ml of dioxane was added carbonyl diimidazole (25.4 g, 156 mmol) in a portionwise manner. The resulting mixture was stirred for about 2.5 hours at room temperature and then stirred at 45° C for 30 minutes. Next, 2-methoxybenzylamine (20.7 ml, 158.7 mmol) was added and the reaction mixture was then stirred for 16 hours at room temperature.

The dioxane was removed under reduced pressure. The product was partitioned between ethyl acetate and water and was washed successively with 1N hydrochloric acid, saturated sodium bicarbonate solution, water, and brine, followed by drying over sodium sulfate and removal of the solvent. Final crystallization from methanol yielded 52.2 g of homogeneous product as yellow crystals. Yield 80.8%. m.p. 157°–160° C.

PREPARATION 2

Synthesis of 2-amino-3-(1H-indol-3-yl)-N-(2-methoxybenzyl)propanamide

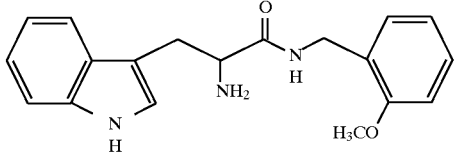

To a mixture of the 2-t-butoxycarbonylamino-3-(1H-indol-3-yl)-N-(2-methoxybenzyl)propanamide prepared supra (25.1 g, 59.2 mmol) and anisole (12 ml, 110.4 mmol) at 0° C. was added dropwise an aqueous solution of trifluoroacetic acid (118 ml, 1.53 mol) in 50 ml of water. This mixture was stirred for one hour at 0° C., followed by stirring for about 2.5 hours at ambient temperature, The mixture was then refrigerated for about 16 hours.

The volatiles were removed under reduced pressure. The product was partition e d between ethyl acetate and saturated sodium bicarbonate solution and was then washed with water followed by brine and then dried over sodium sulfate. The solvents were removed in vacuo. Recrystallization from a 1:1 diethyl ether/cyclohexane solution yielded 18.0 g (94.2%) of homogeneous product as an off-white powder. m.p. 104°–108° C.

PREPARATION 3

Preparation of 3-(1H-indol-3-yl)-2-(N-triphenylmethylamino)propanoic acid [N-trityltryptophan]

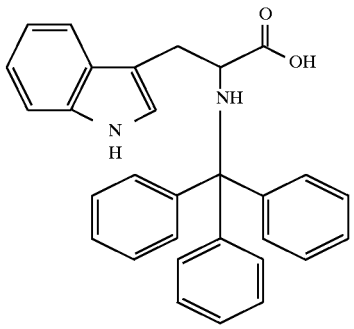

Chlorotrimethylsilane (70.0 ml, 0.527 mol) was added at a moderate rate to a stirring slurry of tryptophan (100.0 g, 0.490 mol) in anhydrous methylene chloride (800 ml) under a nitrogen atmosphere. This mixture was continuously stirred for 4.25 hours. Triethylamine (147.0 ml, 1.055 mol) was added followed by the addition of a solution of triphenylmethyl chloride (147.0 g, 0.552 mol) in methylene chloride (400 ml) using an addition funnel. The mixture was stirred at room temperature, under a nitrogen atmosphere for at least 20 hours. The reaction was quenched by the addition of methanol (500 ml).

The solution was concentrated on a rotary evaporator to near dryness and the mixture was redissolved in methylene chloride and ethyl acetate. An aqueous work-up involving a 5% citric acid solution (2×) and brine (2×) was then performed. The organic layer was dried over anhydrous sodium sulfate, filtered, and concentrated to dryness on a rotary evaporator. The solid was dissolved in hot diethyl ether followed by the addition of hexanes to promote crystallization. By this process 173.6 g (0.389 mol) of analytically pure 3-(1H-indol-3-yl)-2-(N-triphenylmethylamino)propanoic acid was isolated as a light tan solid in two crops giving a total of 79% yield.

PREPARATION 4

Preparation of 3-(1H-indol-3-yl)-N-(2-methoxybenzyl)-2-(N-triphenylmethylamino) propanamide

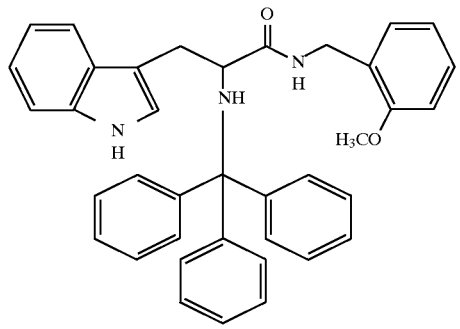

To a stirring solution of 3-(1H-indol-3-yl)-2-(N-triphenylmethylamino)propanoic acid (179.8 g, 0.403 mol), 2-methoxybenzylamine (56.0 ml, 0.429 mol), and hydroxybenzotriazole hydrate (57.97 g, 0.429 mol) in anhydrous tetrahydrofuran (1.7 L) and anhydrous N,N-dimethylformamide (500 ml) under a nitrogen atmosphere at 0C, were added triethylamine (60.0 ml, 0.430 mol) and 1-(3-dimethylaminopropyl)-3-ethoxycarbodiimide hydrochloride (82.25 g, 0.429 mol). The mixture was allowed to warm to room temperature under a nitrogen atmosphere for at least 20 hours. The mixture was concentrated on a rotary evaporator and then redissolved in methylene chloride and an aqueous work-up of 5% citric acid solution (2×), saturated sodium bicarbonate solution (2×), and brine (2×) was performed. The organic layer was dried over anhydrous sodium sulfate, filtered, and concentrated to dryness on a rotary evaporator. The title product was then filtered as a pink solid in two lots. Isolated 215.8 g (0.381 mol) of analytically pure material (95% yield).

Analysis for $C_{38}H_{35}N_3O_2$: Theory: C, 80.68; H, 6.24; N, 7.43. Found: C, 80.58; H, 6.42; N, 7.45.

PREPARATION 5

Preparation of 2-amino-3-(1H-indol-3-yl)-N-(2-methoxybenzyl)propanamide

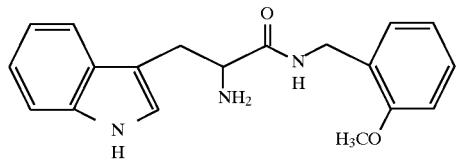

Formic acid (9.0 ml, 238.540 mmol) was added to a stirring solution of 3-(1H-indol-3-yl)-N-(2-methoxybenzyl)-2-(N-triphenylmethylamino)propanamide (14.11 g, 23.763 mmol) in anhydrous methylene chloride under a nitrogen atmosphere at 0° C.

After 4 hours, the reaction mixture was concentrated to an oil on a rotary evaporator and redissolved in diethyl ether and 1.0N hydrochloric acid. The aqueous layer was washed twice with diethyl ether and basified with sodium hydroxide to a pH greater than 12. The product was extracted out with methylene chloride (4×). The organic extracts were combined, dried over anhydrous sodium sulfate, filtered, and concentrated on a rotary evaporator to a white foam. The compound 3-(1H-indol-3-yl)-2-amino-N-(2-methoxybenzyl)propanamide (7.52 g, 21.397 mmols) was isolated giving a 90% yield. No further purification was necessary.

Analysis for $C_{19}H_{21}N_3O_2$: Theory: C, 73.76; H, 7.49; N, 13.58. Found: C, 72.15; H, 7.78; N, 12.77.

PREPARATION 6

Preparation of 2-amino-3-(1H-indol-3-yl)-N-(2-chlorobenzyl)propanamide

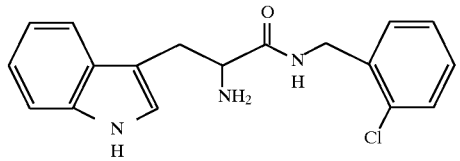

The title compound is prepared essentially as described above in Preparations 4 and 5 except that 2-chlorobenzylamine is employed instead of 2-methoxybenzylamine.

PREPARATION 7

Preparation of 2-t-butoxycarbonylamino-3-(1H-indol-3-yl)-N-(2-chlorobenzyl)propanamide

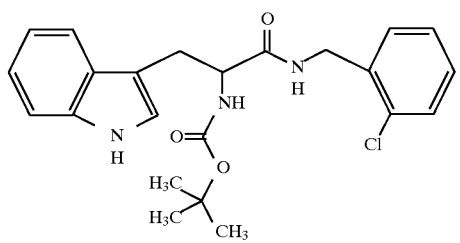

To a solution of N-(t-butoxycarbonyl)tryptophan (21.28 g, 70 mmol) in 140 ml of acetone was added triethylamine (9.76 ml, 7.08 g, 70 mmol) in a portionwise manner. The resulting mixture was stirred for about thirty-five minutes at room temperature and then stirred at 45° C. for 30 minutes under nitrogen. To the resulting mixture ethyl chloroformate (7.35 ml, 8.36 g, 77 mmol) was added with continued cooling and the reaction mixture was stirred for about one hour. Next, 2-chlorobenzylamine (9.30 ml, 10.9 g, 77 mmol) was added and the reaction mixture was then stirred until a white precipitate formed. The ice bath was removed and additional acetone was added. The reaction mixture was then stirred overnight.

The acetone was removed under reduced pressure. The residue was taken up in ethyl acetate (not all was soluble) and washed with dilute hydrochloric acid, followed by sodium hydroxide and then water. The solvents were removed by vacuum. After the addition of ether the reaction product was filtered and was washed with ether. Additional product was obtained by evaporating the ether filtrate. Yield >99%. NMR was consistent with the desired title product.

PREPARATION 8

Preparation of 2-amino-3-(1H-indol-3-yl)-N-(2-chlorobenzyl)propanamide

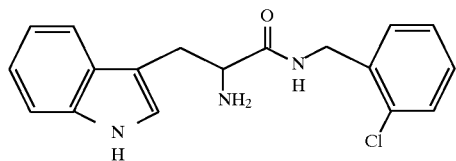

A stirring solution of 2-t-butoxycarbonylamino-3-(1H-indol-3-yl)-N-(2-chlorobenzyl)propanamide (6.00 g, 14 mmol) in 30 ml of 70% aqueous trifluoroacetic acid (21 ml trifluoroacetic acid, 9 ml water) was allowed to stir overnight at room temperature. The progress of this deprotection reaction was monitored by thin layer chromatography.

The solvents were removed in vacuo and the residue was taken up in acetonitrile, which was then removed by vacuum. The residue was partitioned between ether and 1N sodium hydroxide. The organic solvent was removed by vacuum and the residue was taken up in methylene chloride. The residue was removed by filtration and washed with additional methylene chloride.

The filtrate and basic washes were combined, extracted with methylene chloride, and dried over sodium sulfate. The solvents were removed in vacuo. Yield 4.3 grams (93%). NMR was consistent with the desired title intermediate.

PREPARATION 9

Preparation of 2-bromoacetamido-3-(1H-indol-3-yl)-N-(2-chlorobenzyl)propanamide

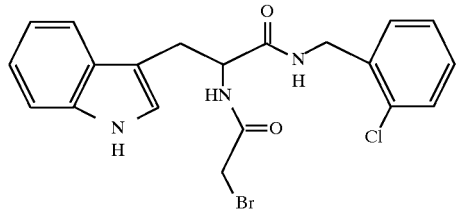

To a stirring solution of 2-amino-3-(1H-indol-3-yl)-N-(2-chlorobenzyl)propanamide (4.39 g, 13.3 mmol) and sodium carbonate (2.73 g, 26.6 mmol) in 100 ml of dry tetrahydrofuran was added bromoacetyl bromide (2.32 ml, 5.37 g, 26.6 mmol). The resulting mixture was then stirred at room temperature for about one hour. The progress of the reaction was monitored by thin layer chromatography.

The reaction mixture was stirred at room temperature overnight after the addition of more bromoacetyl bromide (about 0.5 ml). After the overnight stirring additional sodium carbonate (2.76 g) and bromoacetyl bromide (0.5 ml) were added and the reaction was stirred an additional five minutes.

The reaction mixture was then poured into 600 ml of ethyl acetate and was washed three times with water, followed by washes with dilute hydrochloric acid, water and brine. The organic fraction was dried over sodium sulfate and the solvents were removed by vacuum. Yield 5.24 g (88%). mp 182°–184° C. The NMR was consistent with the desired title intermediate.

PREPARATION 10

Preparation of 2-chloroacetamido-3-(1H-indol-3-yl)-N-(2-chlorobenzyl)propanamide

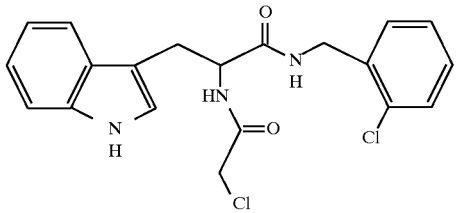

The title intermediate is prepared essentially as described in Preparation 9, supra, except that chloroacetyl chloride is employed in place of bromoacetyl bromide. mp 175–177.

Analysis for $C_{20}H_{19}Cl_2N_3O_2$: Theory: C, 59.42; H, 4.74; N, 10.39. Found: C, 59.21; H, 4.60; N, 10.12.

PREPARATION 11

Preparation of 2,5-dioxo-1,4-piperazinediacetic acid bis (1,1-dimethylethyl) ester and 2,5-dioxo-1-piperazineacetic acid 1,1-dimethylethyl ester

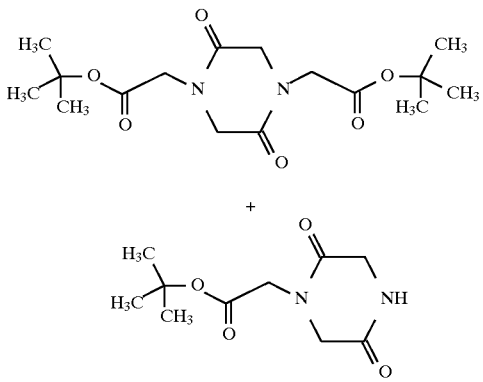

In a two liter round bottom flask, sodium hydride (60% dispersion in mineral oil, 24 g, 0.1 mol) was added to a slurry of glycine anhydride (11.4 g, 0.1 mol) in 1000 ml of N,N-dimethylformamide. The reaction was stirred for about six hours.

To the resulting mixture was then added t-butylbromoacetate (16.14 ml, 0.1 ml) in three portions. The resulting mixture was then stirred overnight at room temperature. The solvents were then removed by evaporation and the residue was taken up in ethyl acetate, and then filtered through CELITE®. The solvents were then removed by evaporation and the residue was extracted several times with hexanes to remove residual mineral oil.

The residue was then extracted with ether and redissolved in methylene chloride. The desired products were further purified and separated from each other by high performance liquid chromatography. mp 152°–153° C.

Analysis for $C_{16}H_{26}N_2O_4$: [2,5-dioxo-1,4-piperazinediacetic acid bis (1,1-dimethylethyl) ester] Theory: C, 56.13; H, 7.65; N, 8.18. Found: C, 56.34; H, 7.46; N, 8.18.

Analysis for $C_{10}H_{16}N_2O_4$: [2,5-dioxo-1-piperazineacetic acid 1,1-dimethylethyl ester] Theory: C, 52.62; H, 7.07; N, 12.27. Found: C, 52.83; H, 7.05; N, 12.20.

PREPARATION 12

Preparation of 2,5-dioxo-1-piperazineacetic acid

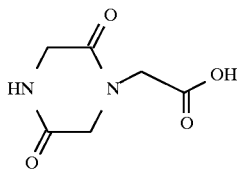

In a 50 ml round bottom flask 5.0 ml of 70% trifluoroacetic acid acid was added to 2,5-dioxo-1-piperazineacetic acid 1,1-dimethylethyl ester (1.0 g) dissolved in anisole (1 ml). The reaction was stirred at room temperature. The progress of the reaction was monitored by thin layer chromatography. The deprotection rection was sufficiently complete after one hour.

The solvents were removed by evaporation. Acetonitrile was twice added to the residue and removed by evaporation. The residue was taken up in acetonitrile, filtered, and washed with acetonitrile. The solvents were removed in vacuo to yield the desired title product. Yield 0.577 g. mp 160° C. IR was consistent with the predicted structure.

Analysis for $C_6H_8N_2O_4$: Theory: C, 41.86; H, 4.68; N, 16.27. Found: C, 41.37; H, 4.53; N, 15.95.

PREPARATION 13

Preparation of ethyl 3-(1H-indol-3-yl)-2-[[(4-benzyl)-2,5-dioxopiperazin-1-yl]methyl]carbonyl]amino]propanoate

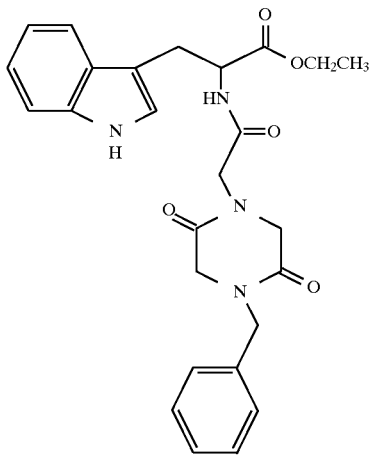

Carbonyldiimidazole (73.8 g, 455 mmol) was dissolved in 1.5 liters of dry acetonitrile. To this was added N-(t-butoxycarbonyl)glycine (80.0 g, 455 mmol) and the resulting mixture was heated at reflux for about thirty minutes. To the resulting mixture was added N-benzylglycine ethyl ester (85 ml, 45 mmol) and the reaction mixture was then heated at reflux overnight. The progress of the reaction was monitored by thin layer chromatography.

The reaction mixture was then stirred an additional 24 hours. The reaction mixture was concentrated in vacuo, and the residue partitioned between ethyl ether and 0.5N hydrochloric acid. The organic fraction was washed with 0.5N hydrochloric acid (three times until the wash was acidic). The organic fraction was then washed twice with a saturated sodium carbonate solution, followed by two washes with brine. The organic fraction was dried over sodium sulfate and the solvents were removed in vacuo to yield 130 grams of N-benzyl-1-[(t-butoxycarbonyl)amino]-N-(ethoxycarbonylmethyl)acetamide as a dark oil.

Trifluoroacetic acid (100 ml) was added to 40 ml of water and cooled to 0° C. The resulting solution was added to neat N-benzyl-1-[(t-butoxycarbonyl)amino]-N-(ethoxycarbonylmethyl)acetamide (130 g, 0.370 mol) and stirred overnight at room temperature. The progress of the reaction was monitored by thin layer chromatography.

An additional 40 ml of 70% trifluoroacetic acid were added and the solution was stirred at room temperature under a nitrogen atmosphere overnight. The solvents were then removed in vacuo. The residue was taken up in 100 ml of acetonitrile. The solvents were again removed in vacuo.

The residue was partitioned between ether and 1N hydrochloric acid. The ether fraction was extracted extensively with 1N hydrochloric acid. The aqueous fraction was basified to pH 12 with 5N sodium hydroxide, resulting in the formation of a white precipitate. The precipitate was removed by filtration, and then washed with water to yield 1-benzyl-2,5-dioxopiperazine (17.14 g, 23%).

In dry tetrahydrofuran (320 ml) was added 1-benzyl-2,5-dioxopiperazine (16.98 g, 83.0 mmol). The resulting slurry was cooled in an acetone/dry ice bath. While stirring under a nitrogen atmosphere, n-butyllithium (57 ml, 91.3 mmol) was added, and the resulting mixture was stirred for 45 minutes. The resulting mixture was then warmed in an ice bath and t-butylbromoacetate (14.7 ml, 91.3 mmol) was added.

The resulting mixture was warmed to room temperature and was refluxed for four hours. The progress of the reaction was monitored by thin layer chromatography.

The solvents were removed in vacuo. The white residue was partitioned between 1N hydrochloric acid and ethyl acetate. The aqueous fraction was washed twice with ethyl acetate. The organic fractions were combined, washed twice with sodium carbonate, twice with brine, and then dried over sodium sulfate. The solvents were removed in vacuo (Fraction I).

The aqueous fraction, supra, was extracted twice with ethylene chloride. The ethylene chloride extract was washed twice with sodium carbonate, twice with brine, and then dried over sodium sulfate. The solvents were removed in vacuo. The residue was triturated with ether to yield Fraction II.

Fraction I and Fraction II were combined to yield 8.7 grams (33%) of 1-benzyl-4-(t-butoxycarbonylmethyl)-2,5-dioxopiperazine.

Trifluoroacetic acid (100 ml of a 70% solution) was cooled in an ice bath under a nitrogen atmosphere and then 1-benzyl-4-(t-butoxycarbonylmethyl)-2,5-dioxopiperazine (8.7 g, 27.4 mmol) was added. The resulting mixture was then allowed to room temperature at which temperature it was stirred for four hours. The progress of the reaction was monitored by thin layer chromatography.

The solvents were removed in vacuo. The residue was dissolved in acetonitrile. The acetonitrile was then removed in vacuo. The deprotected intermediate, 1-[4-benzyl-2,5-dioxopiperazin-1-yl]acetic acid (5.54 g, 77%), was recrystallized from acetonitrile.

1-[4-Benzyl-2,5-dioxopiperazin-1-yl]acetic acid (5.32 g, 20 mmol) was dissolved in 350 ml tetrahydrofuran under a nitrogen atmosphere. To this solution was added DL-tryptophan ethyl ester (5.38 g, 20 mmol), followed by hydroxybenztriazole hydrate (2.97 g, 22 mmol) and triethylamine (3.67 ml, 22 mmol). The resulting mixture was then cooled to 0° C. and 1-ethyl-3-[3-dimethylamino)propyl]carbodiimide hydrochloride (4.3 g, 22 mmol) was added, resulting in the formation of a precipitate. An additional 350 ml of tetrahydrofuran was added to re-dissolve the precipitate.

The reaction mixture slowly warmed to room temperature as the ice bath melted, and the reaction mixture was stirred overnight and the progress of the reaction was monitored by thin layer chromatography. An additional 1.4 grams of the tryptophan ethyl ester was added and the resulting reacton mixture was then allowed to stir overnight at room temperature.

The raction mixture was concentrated in vacuo and then washed twice with a saturated sodium carbonate solution, twice with brine, and then dried over sodium sulfate. The solvents were removed in vacuo. The desired product was further purified by liquid chromatography. Some of the fractions were further purified by dissolving in ethylene chloride, washed twice with 1N hydrochloric acid, twice with brine, and then dried over sodium sulfate. The solvents were removed in vacuo to yield 4.68 grams (98%) of the desired title product, ethyl 3-(1H-indol-3-yl)-2-[[(4-benzyl)-2,5-dioxopiperazin-1-yl]methyl]carbonyl]amino]propanoate. mp 87.8°–89.0° C. NMR was consistent with the desired title product.

FDMS 476 (M+).

Analysis for $C_{26}H_{28}N_4O_5$: Theory: C, 65.53; H, 5.92; N, 11.76. Found: C, 65.83; H, 6.00; N, 11.94.

PREPARATION 14

Preparation of 3-(1H-indol-3-yl)-2-[(4-phenylpiperazin-1-yl)acetamido]propanoic acid

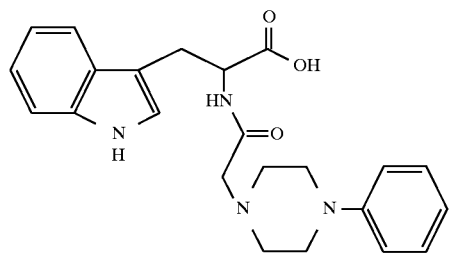

In a one liter round bottom flask under a nitrogen atmosphere were mixed DL-tryptophan (20.4 mg, 0.10 mol) and potassium carbonate (13.8 mg, 0.10 mol) in 500 ml dry tetrahydrofuran. To the resulting slurry, which was cooled in an ice bath, bromoacetylbromide (8.72 ml, 20.2 mg, 0.10 mol) was added portionwise over about fifteen minutes. The resulting mixture was then allowed to warm to room temperature with continued stirring. The progress of the reaction was monitored by thin layer chromatography.

The solvents were removed in vacuo. The residue was then partitioned between water and ethyl acetate. The aqueous fraction was neutralized by the addition of 5N hydrochloric acid. The aqueous fraction was then extracted thrice with ethyl acetate. The organic fractions were combined, washed with brine, and then dried over sodium sulfate. The solvents were removed in vacuo to yield an oil. The desired intermediate, (+−)-α-(bromoacetyl)tryptophan, was then recrystallized from chloroform. mp 135°–136° C.

Analysis for $C_{13}H_{13}BrN_2O_3$: Theory: C, 48.02; H, 4.03; N, 8.61. Found: C, 47.82; H, 4.05; N, 8.40.

In 200 ml of tetrahydrofuran in a 500 ml round bottom flask under a nitrogen atmosphere was added (+−)-α-(bromoacetyl)tryptophan (3.25 mg, 0.01 mol), followed by 4-phenylpiperazine (3.24 mg, 3.1 ml, 0.02 mol), added portionwise over five minutes. Three minutes after addition of the 4-phenylpiperazine, a precipitate formed. The reaction mixture was stirred at room temperature for about 18 hours.

The precipitate was removed by filtration and washed with ether. The filtrate was evaporated. To the evaporated filtrate, sodium hydroxide (12.6 ml of a 1N solution) was added. The resulting mixture was extracted twice with ether. The aqueous fraction was acidified by the addition of 13.6 ml of 1N hydrochloric acid. This aqueous fraction was then extracted thrice with ethanol. The organic fractions were combined and extracted with brine. The solvents were removed in vacuo. The desired title intermediate was recrystallized from chloroform. mp 193°–194° C. FDMS 406, 407, 408.

Analysis for $C_{23}H_{26}N_4O_3$: Theory: C, 67.96; H, 6.45; N, 13.78. Found: C, 66.86; H, 6.34; N, 13.46.

PREPARATION 15

Preparation of 3-(1H-indol-3-yl)-2-[(4-cyclohexylpiperazin-1-yl)acetamido]propanoic acid

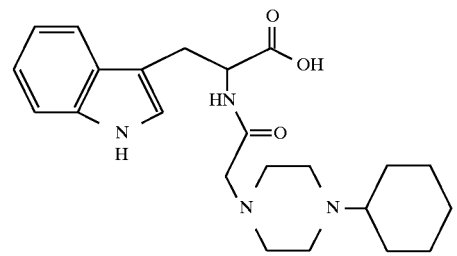

The title product is prepared essentially as described in Preparation 14, supra, except that an equimolar amount of 4-cyclohexylpiperazine is employed instead of the 4-phenylpiperazine employed therein.

PREPARATION 16

Preparation of 3-(1H-indol-3-yl)-2-[[4-(piperidin-1-yl)piperidin-1-yl]acetamido]propanoic acid

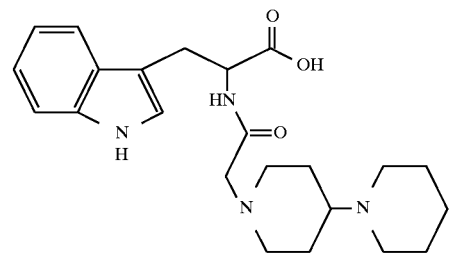

The title product is prepared essentially as described in Preparation 14, supra, except that an equimolar amount of 4-(piperidin-1-yl)piperidine is employed instead of the 4-phenylpiperazine employed therein.

PREPARATION 17

Preparation of 3-(1H-indol-3-yl)-2-[[(4-benzyl)-2,5-dioxopiperazin-1-yl]methyl]carbonyl]amino]propanoic acid

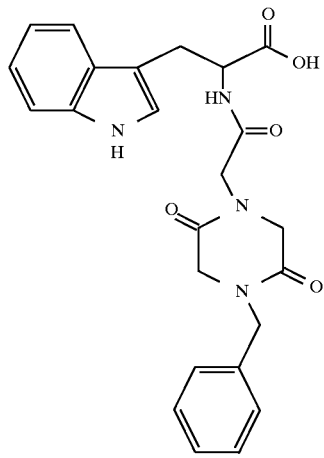

In a 100 ml round bottom flask ethyl 3-(1H-indol-3-yl)-2-[[(4-benzyl)-2,5-dioxopiperazin-1-yl]methyl]carbonyl]amino]propanoate (8.63 g, 18.0 mmol) was dissolved in 300 ml of methanol. Aqueous sodium hydroxide (18 ml of a 5N solution, 90 mmol) was added and the solution was stirred under nitrogen atmosphere for about three hours. The progress of the reaction was monitored by thin layer chromatography.

The solution was acidified to pH 1.0 with 1N hydrochloric acid and was then extracted extensively with chloroform. The solvents were removed in vacuo to yield 7.18 grams (89%) of the desired title intermediate.

FDMS 448 (M+). mp 219°–220° C.

$^1$H NMR: DMSO δ 2.97 (dd, J=8, 15Hz, 1H), 3.13 (dd, J=5, 14 Hz, 1H), 3.85 (s, 2H), 3.85–4.01 (m, 4H), 4.40–4.60 (m, 3H), 6.80–7.10 (m, 3H), 7.20–7.45 (m, 6H), 7.50 (d, J=8 Hz, 1H), 8.34 (d, J=8 Hz, 1H), 10.83 (s, 1H), 12.65 (brs, 1H).

Analysis for $C_{24}H_{24}N_4O_5$: Theory: C, 64.28; H, 5.39; N, 12.49. Found: C, 64.50; H, 5.37; N, 12.74.

EXAMPLE 1

Preparation of N-(2-chlorobenzyl)-3-(1H-indol-3-yl)-2-[(4-benzylpiperlidin-1-yl)acetyl]amino]propanamide hydrochloride salt

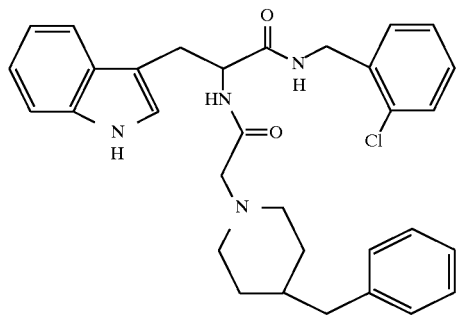

To a stirring solution of 2-bromoacetamido-3-(1H-indol-3-yl)-N-(2-chlorobenzyl)propanamide (0.897 g, 2 mmol) in 40 ml of tetrahydrofuran was added 4-benzylpiperidine (0.70 ml, 0.70 g, 4 mmol). The resulting mixture was stirred at room temperature as the progress of the reaction was monitored by thin layer chromatography. After about 1.75 hours, ether was added to the reaction mixture and the organic fraction was washed with water, dilute sodium carbonate, water, and then brine sequentially.

The organic fraction was dried over sodium sulfate and the solvents were removed in vacuo to yield 1.17 grams of a foam. To this foam were added ethanol and 4 ml of 1N hydrochloric acid. The resulting mixture was filtered and washed with ether. To the residue was added methylene chloride. The resulting crystals were removed by filtration and washed with methylene chloride to yield 0.92 g (79%) of the desired title product. mp 189°–190° C. FDMS 543, 545, 546, 547. NMR was consistent with the desired title product.

Analysis for $C_{32}H_{35}ClN_4O_2 \cdot HCl$: Theory: C, 66.32; H, 6.26; N, 9.67. Found: C, 66.54; H, 6.33; N, 9.35.

EXAMPLE 2

Preparation of N-(2-chlorobenzyl)-3-(1H-indol-3-yl)-2-[(2,5-dioxopiperazin-1-yl)methyl]carbonyl]amino]propanamide

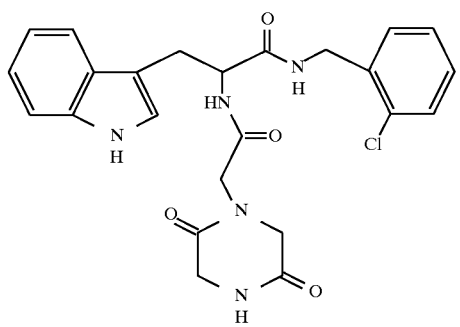

The acid prepared in Preparation 12 (96 mg, 5.58 mmol) is admixed with carbonyldiimidazole (91 mg, 5.58 mmol) in the presence of acetonitrile (20 ml) and dioxane (10 ml). The resulting mixture was then stirred for about thirty minutes. To this mixture was then added 2-amino-3-(1H-indol-3-yl)-N-(2-chlorobenzyl)propanamide (0.183 g, 5.58 mmol). The resulting mixture was heated to reflux and allowed to reflux overnight.

The solvents were then removed in vacuo. Ethyl acetate was then added and the resulting mixture was filtered. The filtrate was washed subsequently with water, dilute hydrochloric acid, water, a concentrated sodium carbonate solution, water, and a saturate sodium chloride solution. The organic fraction was dried over sodium sulfate and filtered. The solvents were removed by vacuum to yield the desired title product. The IR, NMR, and UV spectra were consistent with the title product.

Analysis for $C_{24}H_{24}N_5O_4Cl$: Theory: C, 59.81; H, 5.02; N, 14.53. Found: C, 59.84; H, 5.03; N, 14.49.

EXAMPLE 3

Preparation of N-benzyl-3-(1H-indol-3-yl)-2-[[(4-benzyl)-2,5-dioxopiperazin-1-yl]methyl]carbonyl]amino]propanamide

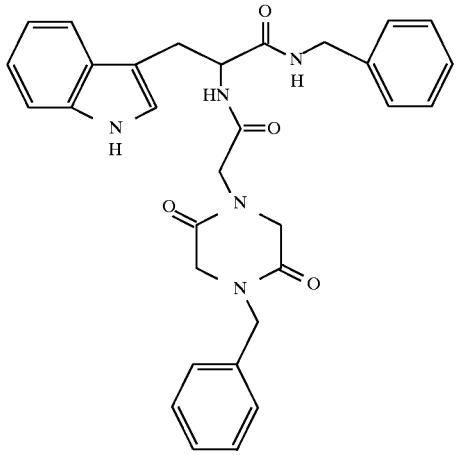

In a 100 ml round bottom flask 3-(1H-indol-3-yl)-2-[[(4-benzyl)-2,5-dioxopiperazin-1-yl]methyl]carbonyl]amino]propanoic acid (0.300 g, 0.67 mmol) was dissolved in 12 ml of dry tetrahydrofuran. To the resulting mixture were added benzylamine (0.088 ml, 0.80 mmol), 1-hydroxybenzotriazole hydrate (0.12 g, 0.87 mmol), and triethylamine (0.12 ml, 0.87 mmol) while stirring under a nitrogen atmosphere. The resulting mixture was then cooled to 0° C. and 1-ethyl-3-[3-(dimethylamino)propyl]carbodiimide hydrochloride (0.17 g, 0.87 mmol) was added.

The resulting mixture was then permitted to warmed to room temperature and was then stirred overnight. The progress of the reaction was monitored by thin layer chromatography.

The reaction mixture was concentrated in vacuo. The residue was dissolved in chloroform, washed twice with 5% aqueous citric acid, and then twice with a saturated sodium carbonate solution. The organic fraction was concentrated by vacuum, and the desired product was further purified by chromatography. Yield (290 mg, 80%). The NMR was consistent with the predicted structure. FDMS (M+) 537. CDCl$_3$ δ 3.17 (dd, J=8, 15 Hz, 1H), 3.33 (dd, J=8, 15 Hz, 1H), 3.46–3.70 (m, 2H), 3.76–4.00 (m, 4H), 4.23 (dd, J=6, 15 Hz, 1H), 4.33 (dd, J=6, 15 Hz, 1H), 4.40–4.56 (m, 2H), 4.80 (m, 1H), 6.55 (br s, 1H), 6.83–6.96 (m, 2H), 6.96–7.40 (m, 13H), 7.63 (d, J=8 Hz, 1H), 8.27 (s, 1H)

Analysis for $C_{31}H_{31}N_5O_4$: Theory: C, 69.26; H, 5.81; N, 13.03. Found: C, 69.23; H, 5.91; N, 12.79.

EXAMPLE 4

Preparation of N-phenyl-3-(1H-indol-3-yl)-2-[[(4-benzyl)-2,5-dioxopiperazin-1-yl]methyl]carbonyl]amino]propanamide

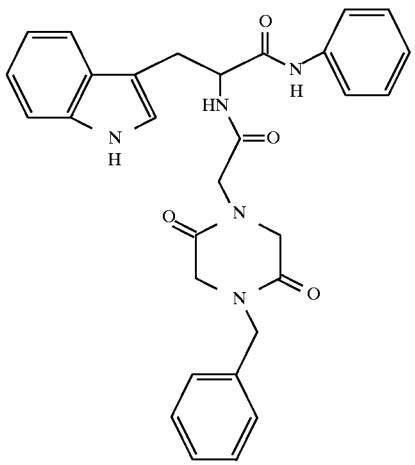

The title compound was prepared essentially as described in Example 3, supra, except that an equimolar amount of aniline was employed instead of benzylamine. Yield (250 mg, 71%). The NMR was consistent with the predicted structure. mp 158.5°–160° C. FDMS (M+) 523.

DMSO δ 3.03 (m, 1H), 3.15 (m, 1H), 3.80–4.10 (m, 6H), 4.50 (s, 2H), 4.68 (m, 1H), 6.90–7.10 (m, 4H), 7.15 (s, 1H), 7.20–7.40 (m, 7H), 7.50–7.70 (m, 3H), 8.46 (d, J=8 Hz, 1H), 10.07 (s, 1H), 10.82 (s, 1H)

Analysis for $C_{30}H_{29}N_5O_4$: Theory: C, 68.82; H, 5.58; N, 13.38. Found: C, 69.04; H, 5.39; N, 13.18.

EXAMPLE 5

Preparation of N-phenylethyl-3-(1H-indol-3-yl)-2-[[(4-benzyl)-2,5-dioxopiperazin-1-yl]methyl]carbonyl]amino]propanamide

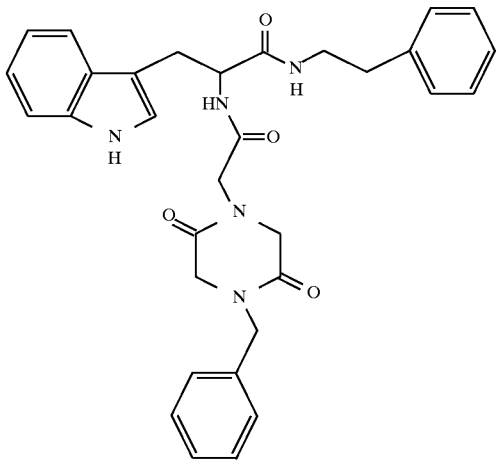

The title compound was prepared essentially as described in Example 3, supra, except that an equimolar amount of 2-phenylethylamine was employed instead of benzylamine. Yield (200 mg, 52%). The NMR was consistent with the predicted structure. FDMS (M+) 551.

Analysis for $C_{32}H_{33}N_5O_4$: Theory: C, 69.67; H, 6.03; N, 12.69. Found: C, 69.56; H, 6.11; N, 12.79.

EXAMPLE 6

Preparation of N-(2-chlorobenzyl)-3-(1H-indol-3-yl)
-2-[[(4-benzyl)-2,5-dioxopiperazin-1-yl]methyl]
carbonyl]amino]propanamide

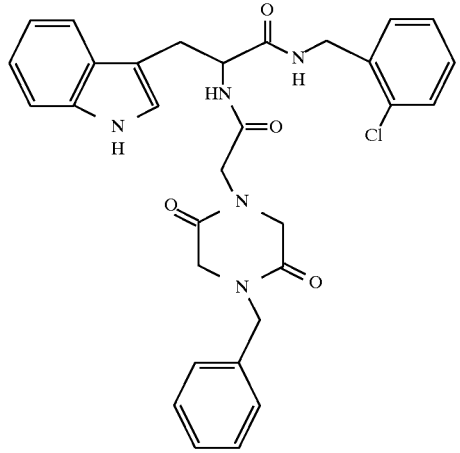

The desired title product was prepared essentially as described in Example 3 except that 2-chlorobenzylamine was employed instead of benzylamine. The NMR was consistent with the predicted structure. mp 214°–215° C. FDMS (M+) 571.

Analysis for $C_{31}H_{30}ClN_5O_4$: Theory: C, 65.09; H, 5.29; N, 12.24. Found: C, 65.65; H, 5.29; N, 12.08.

EXAMPLE 7

Preparation of N-(2-chlorobenzyl)-3-(1H-indol-3-yl)
-2-[(piperidin-1-yl)acetyl]aminolpropanamide

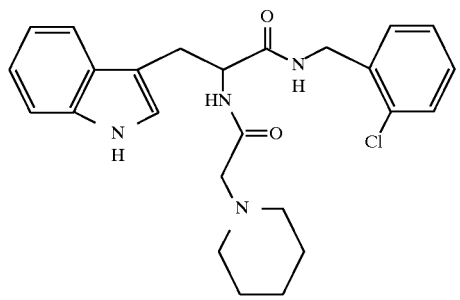

To a stirring solution of 2-bromoacetamido-3-(1H-indol-3-yl)-N-(2-chlorobenzyl)propanamide (0.897 g, 2 mmol) in 40 ml of tetrahydrofuran were added piperidine hydrochloride (0.486 g, 4 mmol) and potassium carbonate (0.55 g, 4 mmol). The resulting mixture was stirred at room temperature as the progress of the reaction was monitored by thin layer chromatography. After about two hours, additional potassium carbonate (0.55 g) and piperidine hydrochloride (0.49 g) were added, the resulting solution was heated to reflux and maintained at that temperature for about 5.5 hours. The reaction mixture was allowed to cool, at which time 2.0 ml of piperidine (free base) was added after which the reaction mixture was stirred for an additional forty minutes.

Ether was then added to the reaction mixture and the organic fraction was washed with water, dilute sodium carbonate, water, and then brine sequentially.

The organic fraction was dried over sodium sulfate and the solvents were removed in vacuo to yield 1.20 grams as a foam. The desired product was further purified by flash chromatography. NMR was consistent with the desired title product.

EXAMPLE 8

Preparation of N-(2-chlorobenzyl)-3-(1H-indol-3-yl)
-2-[(4-methylpiperazin-1-yl)acetyl]
aminolpropanamide

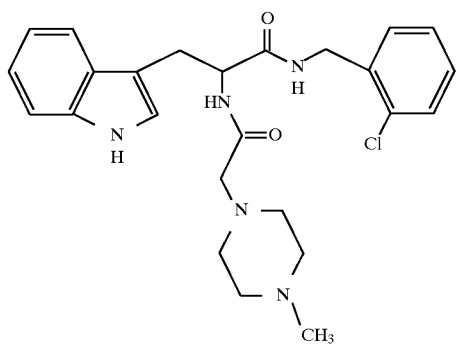

The title compound is prepared essentially as described in Example 7, supra, except that N-methylpiperazine is employed in place of piperidine hydrochloride. mp 186°–187° C. Yield 0.72 g (77%). NMR, IR, and UV were consistent with the proposed title structure. FDMS 466,468, 469.

Analysis for $C_{25}H_{30}ClN_5O_2$: Theory: C, 64.16; H, 6.46; N, 14.96. Found: C, 63.86; H, 6.46; N, 14.66.

EXAMPLE 9

Preparation of N-(2-chlorobenzyl)-3-(1H-indol-3-yl)
-2-[(4-phenylpiperazin-1-yl)acetyl]amino]
propanamide

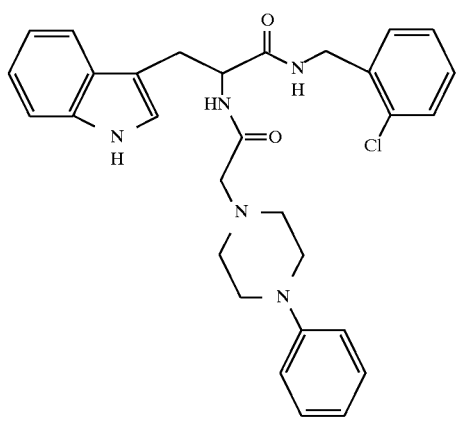

The title compound is prepared essentially as described in Example 7, supra, except that N-phenylpiperazine is employed in place of piperidine hydrochloride. mp 150°–155° C. Yield 0.68 g (63%). NMR, IR, and UV were consistent with the proposed title structure. FDMS 529, 531.

Analysis for $C_{30}H_{32}ClN_5O_2$: Theory: C, 67.98; H, 6.07; N, 13.21. Found: C, 67.77; H, 6.08; N, 12.96.

EXAMPLE 10

Preparation of N-(2-chlorobenzyl)-3-(1H-indol-3-yl)
-2-[(4-phenylpiperidin-1-yl)acetyl]amino]
propanamide

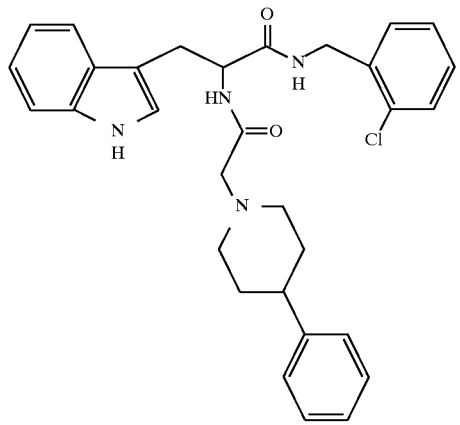

The title compound is prepared essentially as described in Example 7, supra, except that 4-phenylpiperidine is employed in place of piperidine hydrochloride. mp 134°–135° C. Yield 0.83 g (86%). NMR, IR, and UV were consistent with the proposed title structure. FDMS 528.

Analysis for $C_{31}H_{33}ClN_4O_2$: Theory: C, 70.37; H, 6.29; N, 10.59. Found: C, 70.07; H, 6.44; N, 10.60.

EXAMPLE 11

Preparation of N-(2-chlorobenzyl)-3-(1H-indol-3-yl)
-2-[(4-cyclohexylpiperazin-1-yl)acetyl]amino]
propanamide

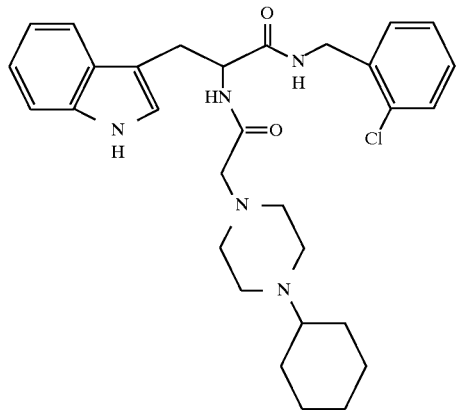

The title compound is prepared essentially as described in Example 7, supra, except that N-cyclohexylpiperazine is employed in place of piperidine hydrochloride. mp 150°–155° C. Yield 0.68 g (63%). NMR, IR, and UV were consistent with the proposed title structure. FDMS 529, 531.

Analysis for $C_{30}H_{32}ClN_5O_2$: Theory: C, 67.98; H, 6.07; N, 13.21. Found: C, 67.77; H, 6.08; N, 12.96.

EXAMPLE 12

Preparation of N-(2-chlorobenzyl)-3-(1H-indol-3-yl)
-2-[[4-(piperidin-1-yl)piperidin-1-yl]acetyl]amino]
propanamide

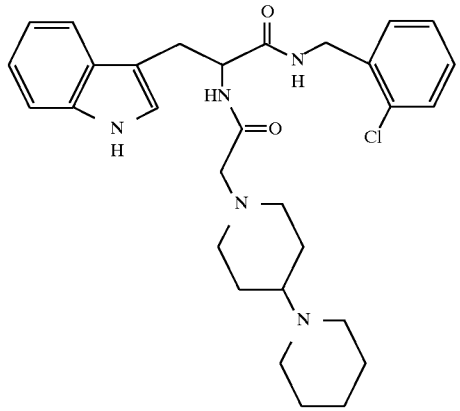

The title compound is prepared essentially as described in Example 7, supra, except that 4-(piperidin-1-yl)piperidine is employed in place of piperidine hydrochloride. mp 134°–135° C. Yield 0.83 g (86%). NMR, IR, and UV were consistent with the proposed title structure. FDMS 528.

EXAMPLE 13

Preparation of N-(2-chlorobenzyl)-3-(1H-indol-3-yl)
-2-[(4-benzylpiperazin-1-yl)acetyl]amino]
propanamide dihydrochloride salt

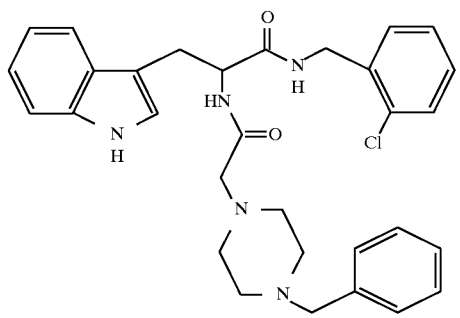

To a stirring solution of 2-chloroacetamido-3-(1H-indol-3-yl)-N-(2-chlorobenzyl)propanamide (0.61 g, 1.49 mmol) in 30 ml of dry tetrahydrofuran was added 1-benzylpiperazine (0.522 ml, 3 mmol). The resulting reaction mixture was stirred at room temperature for about 16 hours. The progress of the reaction was monitored by thin layer chromatography.

The reaction mixture was then warmed for one hour and then heated to reflux, at which temperature the reaction mixture was maintained for about 3.5 hours. The solvents were removed in vacuo, and the residue was taken up in a 1:1 ether:ethyl acetate mixture, which was washed with dilute hydrochloric acid. These acidic extracts were combined and basified with sodium carbonate. This was then extracted four times with ethyl acetate. These organic fractions were combined, washed with brine, and dried over sodium sulfate.

The dihydrochloride salt was made by the addition of dilute hydrochloride acid (5 ml) to the free base in ethanol.

The solvents were removed in vacuo and the crystals were harvested by filtration, and then washed with ethanol. Yield 0.85 grams. mp 205°–210° C. NMR and IR were consistent with proposed title compounds.

Analysis for $C_{31}H_{34}ClN_5O_2 \cdot 2HCl$: Theory: C, 60.35; H, 5.88; N, 11.35. Found: C, 60.45; H, 6.10; N, 11.58.

EXAMPLE 14

Preparation of N-(2-methoxybenzyl)-3-(1H-indol-3-yl)-2-[(4-phenylpiperazin-1-yl)acetyl]aminolpropanamide

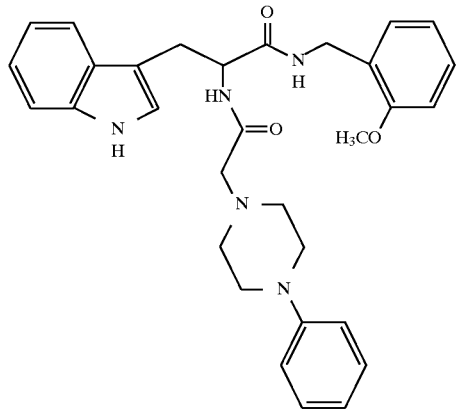

A stirring solution of 3-(1H-indol-3-yl)-2-[(4-phenylpiperazin-1-yl)acetamido]propanoic acid (0.41 g, 1 mmol), prepared as described in Preparation 14 supra, in 25 ml of dioxane was heated and carbonyldiimidazole (0.16 g, 1 mmol) was added. The resulting mixture was heated until all materials were dissolved. At that time 2-methoxybenzylamine (0.108 ml, 0.14 g, 1 mmol) was added. The resulting mixture was heated for one hour. The progress of the reaction was monitored by thin layer chromatography.

After the reaction was substantially complete, the solvents were removed in vacuo. The residue was partitioned between ethyl acetate and water. The organic fraction was washed sequentially with water, a sodium carbonate solution, twice with water, and then brine. The organic fraction was then dried over sodium sulfate and the solvents were removed in vacuo.

The desired title product was further purified by flash chromatography to yield 0.214 grams. mp 172–174. FDMS 525. IR and UV were consistent with the desired title product.

Analysis for $C_{31}H_{35}N_5O_3$: Theory: C, 70.83; H, 6.71; N, 13.32. Found: C, 71.09; H, 6.89; N, 13.04.

EXAMPLE 15

Preparation of N-benzyl-N-methyl-3-(1H-indol-3-yl)-2-[(4-phenylpiperazin-1-yl)acetyl]amino]propanamide

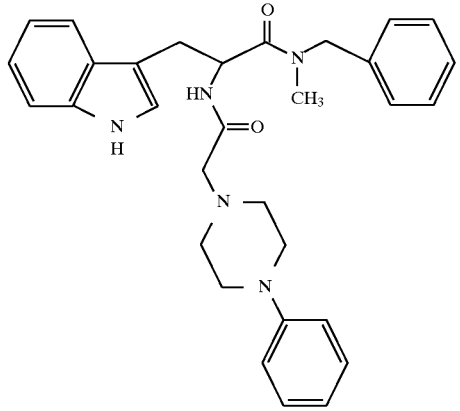

The desired title product was prepared essentially as described in Example 14, supra, except that an equimolar amount of N-benzylmethylamine was employed in place of the 2-methoxybenzylamine employed therein.

FDMS 509. NMR and UV were consistent with the above title structure.

Analysis for $C_{31}H_{35}N_5O_2$: Theory: C, 73.06; H, 6.92; N, 13.74. Found: C, 72.78; H, 6.95; N, 13.88.

EXAMPLE 16

Preparation of N-benzyl-3-(1H-indol-3-yl)-2-[(4-phenylpiperazin-1-yl)acetyl]amino]propanamide

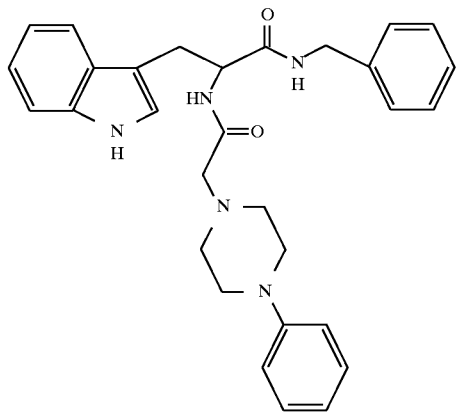

The desired title product was prepared essentially as described in Example 14, supra, except that an equimolar amount of benzylamine was employed in place of the 2-methoxybenzylamine employed therein.

FDMS 495. mp 154°–156° C. NMR, UV, and IR were consistent with the above title structure.

Analysis for $C_{30}H_{33}N_5O_2$: Theory: C, 72.70; H, 6.71; N, 14.31. Found: C, 72.52; H, 6.60; N, 13.93.

EXAMPLE 17

Preparation of N-(4-chlorobenzyl)-3-(1H-indol-3-yl)-2-[(4-phenylpiperazin-1-yl)acetyl]amino]propanamide

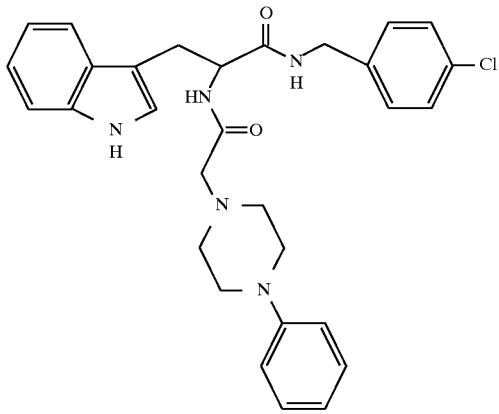

The desired title product was prepared essentially as described in Example 14, supra, except that an equimolar amount of 4-chlorobenzylamine was employed in place of the 2-methoxybenzylamine employed therein.

FDMS 529. mp 204°–205° C. NMR, IR, and UV were consistent with the above title structure.

Analysis for $C_{30}H_{35}ClN_5O_2$: Theory: C, 67.98; H, 6.09; N, 13.21. Found: C, 68.05; H, 6.22; N, 13.06.

EXAMPLE 18

Preparation of N-(2-chlorobenzyl)-3-(1H-indol-3-yl)-2-[[(4-methyl)-2,5-dioxopiperazin-1-yl]methyl]carbonyl]amino]propanamide

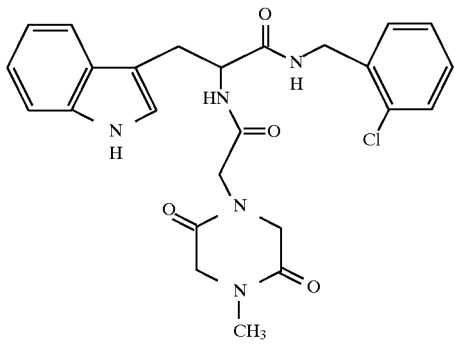

The desired title product was prepared essentially as described in Example 6 except that an equimolar amount of 3-(1H-indol-3-yl)-2-[(4-methyl-2,5-dioxopiperazin-1-yl)methyl]carbonyl]amino]propanoic acid was employed instead of the 3-(1H-indol-3-yl)-2-[(4-benzyl-2,5-dioxopiperazin-1-yl)methyl]carbonyl]amino]propanoic acid employed therein The NMR was consistent with the predicted structure. mp 197°–198° C. FDMS (M+) 495, 497, 498.

Analysis for $C_{25}H_{26}ClN_5O_4$: Theory: C, 60.54; H, 5.28; N, 14.12. Found: C, 60.83; H, 5.43; N, 14.29.

The biological activity of the compounds employed the present invention may be measured by a number of methods known to those skilled in the art, including those described in the patents and scientific literature described supra.

The growth hormone secretagogues of Formula I are useful in vitro as unique tools for understanding how growth hormone secretion is regulated at the pituitary level. This includes use in the evaluation of many factors thought or known to influence growth hormone secretion, such as age, sex, nutritional factors, glucose, amino acids, fatty acids, as well as fasting and non-fasting states. In addition, the compounds employed in this invention can be used in the evaluation of how other hormones modify growth hormone releasing activity. For example, it has already been established that somatostatin inhibits growth hormone release.

Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I can also be employed to investigate the possible negative or positive feedback effects of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep, and the like to accelerate and increase their rate and extent of growth, to improve feed efficiency, and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone.

Comparison of the amounts of growth hormone in each of these samples would be a means for directly determining the ability of the patient's pituitary to release growth hormone.

The present invention generally employs at least one of the compounds of Formula I in association with a pharmaceutical carrier or diluent. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a corticosteroid to minimize the catabolic side effects or with other pharmaceutically active materials wherein the combination enhances efficacy and minimizes side effects. Growth promoting and anabolic agents include, but are not limited to, TRH, diethylstilbesterol, estrogens, β-agonists, theophylline, anabolic steroids, enkephalins, E series prostaglandins, compounds disclosed in U.S. Pat. No. 3,239, 345, e.g., zeranol, and compounds disclosed in U.S. Pat. No. 4,036,979, e.g., sulbenox, or peptides disclosed in U.S. Pat. No. 4,411,890.

A still further use of the growth hormone secretagogues of this invention is in combination with other growth hormone secretagogues such as the growth hormone releasing peptides GHRP-6, GHRP-1 as described in U.S. Pat. No. 4,411,890 and Patent Cooperation Treaty Publications WO 89/07110 and WO 89/07111, as well as hexarelin and the newly discovered GHRP-2 as described in Patent Cooperation Treaty Publication WO 93/04081; or growth hormone releasing hormone and its analogs; or growth hormone and its analogs; or somatomedins including IGF-1 and IGF-2; or α-adrenergic agonists, such as clonidine; or serotonin 5-HT$_1$D agonists, such as sumatriptan; or agents which inhibit somatostatin or its release, such as physostigmine and pyridostigmine.

As is well known to those skilled in the art, the known and potential uses of growth hormone are varied and multitudinous. The administration of the compounds employed in the present invention for the purpose of stimulating the release of endogenous growth hormone can have the same effects or uses as growth hormone itself. These varied uses of growth hormone may be summarized as follows: stimulating growth hormone release in elderly humans; treating growth hormone deficient adults; prevention of catabolic side effects of glucocorticoids; treatment of osteoporosis; stimulation of the immune system; acceleration of wound healing; accelerating bone fracture repair; treatment of growth retardation; treating acute or chronic renal failure or insufficiency; treatment of physiological short stature, including growth hormone deficient children; treating short stature associated with chronic illness; treatment of obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, skeletal dysplasia, hypercortisonism, and Cushings syndrome; replacement of growth hormone in stressed patients; treatment of osteochondrodysplasias, Noonans syndrome, sleep disorders, Alzheimer's disease, delayed wound healing, and psychosocial deprivation; treatment of pulmonary dysfunction and ventilator dependency; attenuation of protein catabolic response after a major operation; treating malabsorption syndromes; reducing cachexia and protein loss due to chronic illness such as cancer or AIDS; accelerating weight gain and portion accretion in patients on total parenteral nutrition; treatment of hyperinsulinemia including nesidioblastosis; adjuvant treatment for ovulation induction and to prevent and treat gastric and duodenal ulcers; to stimulate thymic development and prevent the age-related decline of thymic function; adjunctive therapy for patients on chronic hemodialysis; treatment of immunosuppressed patients and to enhance antibody response following vaccination; improvement in muscle strength, mobility, maintenance of skin thickness, metabolic homeostasis, renal homeostasis in the frail elderly; stimulation of osteoblasts, bone remodeling, and cartilage growth; treatment of neurological diseases such as peripheral and drug-induced neuropathy, Guillan-Barre syndrome, amyotrophic lateral sclerosis, multiple sclerosis, cerebrovascular accidents, and demyelinating diseases; stimulation of the immune system in companion animals and treatment of disorders of aging in companion animals; growth promotion in livestock; and stimulation of wool growth in sheep.

It will be understood by those skilled in the art that there are numerous compounds now being used in an effort to treat the diseases or therapeutic indications enumerated above. Combinations of these therapeutic agents, some of which have also been mentioned above, with the growth hormone secretagogues employed in this invention will bring additional, complementary, and often synergistic properties to enhance the growth promotant, anabolic, and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

The compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The present invention also includes methods employing pharmaceutical compositions which contain, as the active ingredient, the compounds of Formula I associated with pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone | 4.0 mg |

-continued

| Ingredient | Quantity (mg/tablet) |
|---|---|
| (as 10% solution in water) | |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) | 50.0 mg |

-continued

| Ingredient | Amount |
|---|---|
| Microcrystalline cellulose (89%) Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water The sodium benzoate, flavor, and color are diluted with some of the water and added with stirring. Sufficient water is then added to produce the required volume.

FORMULATION EXAMPLE 8

Capsules, each containing 15 mg of medicament, are made as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

FORMULATION EXAMPLE 9

An intravenous formulation may be prepared as follows:

| Ingredient | Quantity |
|---|---|
| Active Ingredient | 250.0 mg |
| Isotonic saline | 1000 ml |

FORMULATION EXAMPLE 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

FORMULATION EXAMPLE 11

Sublingual or buccal tablets, each containing 10 mg of active ingredient, may be prepared as follows:

| Ingredient | Quantity Per Tablet |
|---|---|
| Active Ingredient | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches").

Such transdermal patches may be used to provide continuous or discontinuous infusion of the compounds of the present invention in controlled amounts. The construction and use of transdermal patches for the delivery of pharmaceutical agents is well known in the art. See e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

We claim:

1. A method for stimulating the secretion of growth hormone in a mammal, which method comprises administering to a mammal in need of said treatment an effective amount of a compound of the formula

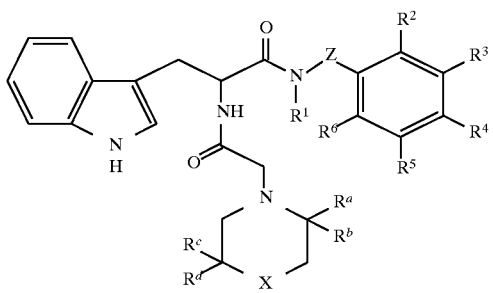

wherein:

$R^1$ is hydrogen, $C_1$–$C_6$ alkyl, or $C_2$–$C_6$ alkanoyl;

$R^2$, $R^3$, $R^4$, $R^5$, and $R^6$ are independently selected from the group consisting of hydrogen, halo, $C_1$–$C_6$ alkyl, $C_1$–$C_6$ alkoxy, $C_1$–$C_6$ alkylamino, $C_1$–$C_6$ alkylthio, amino, and trifluoromethyl;

$R^a$ and $R^b$ are each hydrogen or together form an oxo group;

$R^c$ and $R^d$ are each hydrogen or together form an oxo group;

Z is a bond or $C_1$–$C_6$ alkylidenyl;

n is 0–6; and

X is

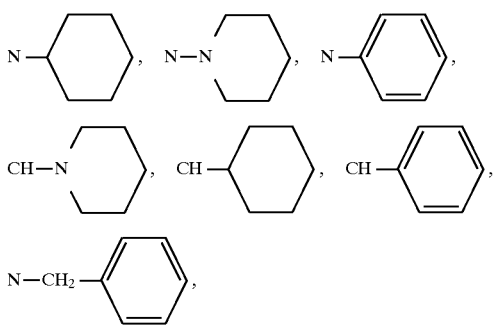

N-$R^7$, CH—N$R^8R^9$, or CH—$R^{10}$ where $R^7$, $R^8$, $R^9$, and $R^{10}$ are independently selected from the group consisting of hydrogen and $C_1$–$C_6$ alkyl;

or a pharmaceutically acceptable salt or solvate thereof.

2. A method as claimed in claim 1 employing a compound wherein $R^a$, $R^b$, $R^c$, and $R^d$ are all hydrogen, or a pharmaceutically acceptable salt or solvate thereof.

3. A method as claimed in claim 2 employing a compound wherein X, when combined to the heterocyclic ring to which it is attached, forms 4-(piperidin-1-yl)piperidinyl-1-yl, 4-cyclohexylpiperazin-1-yl, 4-phenylpiperazin-1-yl, 4-phenylpiperidin-1-yl, 4-(N,N-dimethylamino)piperidin-1-yl, or 4-(N,N-diethylamino)piperidin-1-yl, or a pharmaceutically acceptable salt or solvate thereof.

4. A method as claimed in claim 3 employing a compound wherein at least one, but not more than three, of $R^2$, $R^3$, $R^4$, $R^5$, and $R^6$ are independently selected from the group consisting of chloro, fluoro, trifluoromethyl, methyl, ethyl, methoxy, ethoxy, methylamine, ethylamine, amino, methylthio, and ethylthio, or a pharmaceutically acceptable salt or solvate thereof.

5. A method as claimed in claim 4 employing a compound wherein $R^1$ is hydrogen, methyl, or acetyl, or a pharmaceutically acceptable salt or solvate thereof.

6. A method as claimed in claim 5 employing a compound selected from the group consisting of N-(2-methoxybenzyl) -3-(1H-indol-3-yl)-2-[[(4-phenylpiperazin-1-yl)acetyl] amino]propanamide, N-(2-ethoxybenzyl)-3-(1H-indol-3-yl) -2-[[(4-phenylpiperazin-1-yl)acetyl]amino]propanamide, N-(2-methylbenzyl)-3-(1H-indol-3-yl)-2-[[(4-phenylpiperazin-1-yl)acetyl]amino]propanamide, N-(2-chlorobenzyl)-3-(1H-indol-3-yl)-2-[[(4-phenylpiperazin-1-yl)acetyl]amino]propanamide, N-(2-trifluoromethylbenzyl)-3-(1H-indol-3-yl)-2-[[(4-phenylpiperazin-1-yl)acetyl]amino]propanamide, N-(2-ethylbenzyl)-3-(1H-indol-3-yl)-2-[[(4-phenylpiperazin-1-yl)acetyl]amino]propanamide, N-(3,4-dimethoxybenzyl)-3-(1H-indol-3-yl)-2-[[(4-phenylpiperazin-1-yl)acetyl]amino]propanamide, N-(3,4-dimethylbenzyl)-3-(1H-indol-3-yl)-2-[[(4-phenylpiperazin-1-yl)acetyl]amino]propanamide, N-(3,4-diethoxybenzyl)-3-(1H-indol-3-yl)-2-[[(4-phenylpiperazin-1-yl)acetyl]amino] propanamide, N-(3,4-diethylbenzyl)-3-(1H-indol-3-yl)-2-[[(4-phenylpiperazin-1-yl)acetyl]amino]propanamide, N-(3,4-dichlorobenzyl)-3-(1H-indol-3-yl)-2-[[(4-phenylpiperazin-1-yl)acetyl]amino]propanamide, N-[3,5-bis(trifluoromethyl)benzyl]-3-(1H-indol-3-yl)-2-[[(4-phenylpiperazin-1-yl)acetyl]amino]propanamide, N-(3,4,5-trimethoxybenzyl)-3-(1H-indol-3-yl)-2-[[(4-phenylpiperazin-1-yl)acetyl]amino]propanamide, N-(3,4,5-trimethylbenzyl)-3-(1H-indol-3-yl)-2-[[(4-phenylpiperazin-1-yl)acetyl]amino]propanamide, N-(3,4,5-triethoxybenzyl)-3-(1H-indol-3-yl)-2-[[(4-phenylpiperazin-1-yl)acetyl]amino]propanamide, N-(3,4,5-triethylbenzyl)-3-(1H-indol-3-yl)-2-[[(4-phenylpiperazin-1-yl)acetyl]amino]propanamide, N-(3,4,5-trichlorobenzyl)-3-(1H-indol-3-yl)-2-[[(4-phenylpiperazin-1-yl)acetyl]amino]propanamide, N-[3,4,5-tri(trifluoromethyl)benzyl]-3-(1H-indol- 3-yl)-2-[[(4-phenylpiperazin-1-yl)acetyl]amino]propanamide, N-(2-methoxybenzyl)-3-(1H-indol-3-yl)-2-[[(4-cyclohexylpiperazin-1-yl)acetyl]amino]propanamide, N-(2-ethoxybenzyl)-3-(1H-indol-3-yl)-2-[[(4-cyclohexylpiperazin-1-yl)acetyl]amino]propanamide, N-(2-methylbenzyl)-3-(1H-indol-3-yl)-2-[[(4-cyclohexylpiperazin-1-yl)acetyl]amino]propanamide, N-(2-chlorobenzyl)-3-(1H-indol-3-yl)-2-[[(4-cyclohexylpiperazin-1-yl)acetyl]amino]propanamide, N-(2-trifluoromethylbenzyl)-3-(1H-indol-3-yl)-2-[[(4-cyclohexylpiperazin-1-yl)acetyl]amino]propanamide, N-(2-ethylbenzyl)-3-(1H-indol-3-yl)-2-[[(4-cyclohexylpiperazin-1-yl)acetyl]amino]propanamide, N-(3,4-dimethoxybenzyl)-3-(1H-indol-3-yl)-2-[[(4-cyclohexylpiperazin-1-yl)acetyl] aminolpropanamide, N-(3,4-dimethylbenzyl)-3-(1H-indol-3-yl)-2-[[(4-cyclohexylpiperazin-1-yl)acetyl]amino] propanamide, N-(3,4-diethoxybenzyl)-3-(1H-indol-3-yl)-2-[[(4-cyclohexylpiperazin-1-yl)acetyl]amino]propanamide, N-(3,4-diethylbenzyl)-3-(1H-indol-3-yl)-2-[[(4-cyclohexylpiperazin-1-yl)acetyl]aminolpropanamide, N-(3,4-dichlorobenzyl)-3-(1H-indol-3-yl)-2-[[(4-cyclohexylpiperazin-1-yl)acetyl]amino]propanamide, N-[3,5-bis(trifluoromethyl)benzyl]-3-(1H-indol-3-yl )-2-[[(4-cyclohexylpiperazin-1-yl )acetyl]amino]propanamide, N-(3,4,5-trimethoxybenzyl)-3-(1H-indol-3-yl)-2-[[(4-cyclohexylpiperazin-1-yl)acetyl]amino]propanamide, N-(3,4,5-trimethylbenzyl)-3-(1H-indol-3-yl)-2-[[(4-cyclohexylpiperazin-1-yl)acetyl]amino]propanamide, N-(3,4,5-triethoxybenzyl)-3-(1H-indol-3-yl)-2-[[(4-cyclohexylpiperazin-1-yl)acetyl]amino]propanamide, N-(3,4,5-triethylbenzyl)-3-(1H-indol-3-yl)-2-[[(4-cyclohexylpiperazin-1-yl)acetyl]amino]propanamide, N-(3,4,5-trichlorobenzyl)-3-(1H-indol-3-yl)-2-[[(4-cyclohexylpiperazin-1-yl)acetyl]aminolpropanamide, N-[3,4,5-tri(trifluoromethyl)benzyl]-3-(1H-indol-3-yl)-2-[[(4-cyclohexylpiperazin-1-yl)acetyl]amino]propanamide, N-(2-methoxybenzyl)-3-(1H-indol-3-yl)-2-[[[4-(piperidin-1-yl)

piperidin-1-yl]acetyl]amino]propanamnide, N-(2-ethoxybenzyl)-3-(1H-indol-3-yl)-2-[[[4-(piperidin-1-yl)piperidin-1-yl]acetyl]amino]propanamide, N-(2-methylbenzyl)-3-(1H-indol-3-yl)-2-[[[4-(piperidin-1-yl)piperidin-1-yl]acetyl]amino]propanamide, N-(2-chlorobenzyl)-3-(1H-indol-3-yl)-2-[[[4-(piperidin-1-yl)piperidin-1-yl]acetyl]amino]propanamide, N-(2-trifluoromethylbenzyl)-3-(1H-indol-3-yl)-2-[[[4-(piperidin-1-yl)piperidin-1-yl]acetyl]amino]propanamide, N-(2-ethylbenzyl)-3-(1H-indol-3-yl)-2-[[[4-(piperidin- 1-yl)piperidin-1-yl]acetyl]amino]propanamide, N-(3,4-dimethoxybenzyl)-3-(1H-indol-3-yl)-2-[[[4-(piperidin-1-yl)piperidin-1-yl]acetyl]amino]propanamide, N-(3,4-dimethylbenzyl)-3-(1H-indol-3-yl)-2-[[[4-(piperidin-1-yl)piperidin-1-yl]acetyl]aminolpropanamide, N-(3,4-diethoxybenzyl)-3-(1H-indol-3-yl)-2-[[[4-(piperidin-1-yl)piperidin-1-yl]acetyl]amino]propanamide, N-(3,4-diethylbenzyl)-3-(1H-indol-3-yl)-2-[[[4-(piperidin-1-yl)piperidin-1-yl]acetyl]amino]propanamide, N-(3,4-dichlorobenzyl)-3-(1H-indol-3-yl)-2-[[[4-(piperidin-1-yl)piperidin 1-yl]acetyl]amino]propanamide, N-[3,5-bis(trifluoromethyl)benzyl]-3-(1H-indol-3-yl)-2-[[[4-(piperidin-1-yl)piperidin-1-yl]acetyl]amino]propanamide, N-(3,4,5-trimethoxybenzyl)-3-(1H-indol-3-yl)-2-[[[4-(piperidin-1-yl)piperidin-1-yl]acetyl]amino]propanamide, N-(3,4,5-trimethylbenzyl)-3-(1H-indol-3-yl)-2-[[[4-(piperidin-1-yl)piperidin-1-yl]acetyl]amino]propanamide, N-(3,4,5-triethoxybenzyl)-3-(1H-indol-3-yl)-2-[[[4-(piperidin-1-yl)piperidin-1-yl]acetyl]amino]propanamide, N-(3,4,5-triethylbenzyl)-3-(1H-indol-3-yl)-2-[[[4-(piperidin-1-yl)piperidin-1-yl]acetyl]amino]propanamide, N-(3,4,5-trichlorobenzyl)-3-(1H-indol-3-yl)-2-[[[4-(piperidin-1-yl)piperidin-1-yl]acetyl]amino]propanamide, N-[3,4,5-tri(trifluoromethyl)benzyl]-3-(1H-indol-3-yl)-2-[[[4-(piperidin-1-yl)piperidin-1-yl]acetyl]amino]propanamide, N-methyl-N-(2-methoxybenzyl)-3-(1H-indol-3-yl)-2-[[(4-phenylpiperazin-1-yl)acetyl]amino]propanamide, N-methyl-N-(2-ethoxybenzyl)-3-(1H-indol-3-yl)-2-[[(4-phenylpiperazin-1-yl)acetyl]amino]propanamide, N-methyl-N-(2-methylbenzyl)-3-(1H-indol-3-yl)-2-[[(4-phenylpiperazin-1-yl)acetyl]amino]propanamide, N-methyl-N-(2-chlorobenzyl)-3-(1H-indol-3-yl)-2-[[(4-phenylpiperazin-1-yl)acetyl]amino]propanamide, N-methyl-N-(2-trifluoromethylbenzyl)-3-(1H-indol-3-yl)-2-[[(4-phenylpiperazin-1-yl)acetyl]amino]propanamide, N-methyl-N-(2-ethylbenzyl)-3-(1H-indol-3-yl)-2-[[(4-phenylpiperazin-1-yl)acetyl]amino]propanamide, N-methyl-N-(3,4-dimethoxybenzyl)-3-(1H-indol-3-yl)-2-[[(4-phenylpiperazin-1-yl)acetyl]amino]propanamide, N-methyl-N-(3,4-dimethylbenzyl)-3-(1H-indol-3-yl)-2-[[(4-phenylpiperazin-1-yl)acetyl]amino]propanamide, N-methyl-N-(3,4-diethoxybenzyl)-3-(1H-indol-3-yl)-2-[[(4-phenylpiperazin-1-yl)acetyl]aminolpropanamide, N-methyl-N-(3,4-diethylbenzyl)-3-(1H-indol-3-yl)-2-[[(4-phenylpiperazin-1-yl)acetyl]amino]propanamide, N-methyl-N-(3,4-dichlorobenzyl)-3-(1H-indol-3-yl)-2-[[(4-phenylpiperazin-1-yl)acetyl]amino]propanamide, N-[3,5-bis(trifluoromethyl)benzyl]-3-(1H-indol-3-yl)-2-[[(4-phenylpiperazin-1-yl)acetyl]amino]propanamide, N-methyl-N-(3,4,5-trimethoxybenzyl)-3-(1H-indol-3-yl)-2-[[(4-phenylpiperazin-1-yl)acetyl]aminolpropanamide, N-methyl-N-(3,4,5-trimethylbenzyl)-3-(1H-indol-3-yl)-2-[[(4-phenylpiperazin-1-yl)acetyl]amino]propanamide, N-methyl-N-(3,4,5-triethoxybenzyl)-3-(1H-indol-3-yl)-2-[[(4-phenylpiperazin-1-yl)acetyl]amino]propanamide, N-methyl-N-(3,4,5-triethylbenzyl)-3-(1H-indol-3-yl)-2-[[(4-phenylpiperazin-1-yl)acetyl]amino]propanamide, N-methyl-N-(3,4,5-trichlorobenzyl)-3-(1H-indol-3-yl)-2-[[(4-phenylpiperazin-1-yl)acetyl]amino]propanamide, N-[3,4,5-tri(trifluoromethyl)benzyl]-3-(1H-indol-3-yl)-2-[[(4-phenylpiperazin-1-yl)acetyl]amino]propanamide, N-methyl-N-(2-methoxybenzyl)-3-(1H-indol-3-yl)-2-[[(4-cyclohexylpiperazin-1-yl)acetyl]amino]propanamide, N-methyl-N-(2-ethoxybenzyl)-3-(1H-indol-3-yl)-2-[[(4-cyclohexylpiperazin-1-yl)acetyl]amino]propanamide, N-methyl-N-(2-methylbenzyl)-3-(1H-indol-3-yl)-2-[[(4-cyclohexylpiperazin-1-yl)acetyl]amino]propanamide, N-methyl-N-(2-chlorobenzyl)-3-(1H-indol-3-yl)-2-[[(4-cyclohexylpiperazin-1-yl)acetyl]amino]propanamide, N-methyl-N-(2-trifluoromethylbenzyl)-3-(1H-indol-3-yl)-2-[[(4-cyclohexylpiperazin-1-yl)acetyl]amino]propanamide, N-methyl-N-(2-ethylbenzyl)-3-(1H-indol-3-yl)-2-[[(4-cyclohexylpiperazin-1-yl)acetyl]amino]propanamide, N-methyl-N-(3,4-dimethoxybenzyl)-3-(1H-indol-3-yl)-2-[[(4-cyclohexylpiperazin-1-yl)acetyl]amino]propanamide, N-methyl-N-(3,4-dimethylbenzyl)-3-(1H-indol-3-yl)-2-[[(4-cyclohexylpiperazin-1-yl)acetyl]amino]propanamide, N-methyl-N-(3,4-diethoxybenzyl)-3-(1H-indol-3-yl)-2-[[(4-cyclohexylpiperazin-1-yl)acetyl]amino]propanamide, N-methyl-N-(3,4-diethylbenzyl)-3-(1H-indol-3-yl)-2-[[(4-cyclohexylpiperazin-1-yl)acetyl]amino]propanamide, N-methyl-N-(3,4-dichlorobenzyl)-3-(1H-indol-3-yl)-2-[[(4-cyclohexylpiperazin-1-yl)acetyl]amino]propanamide, N-[3,5-bis(trifluoromethyl)benzyl]-3-(1H-indol-3-yl)-2-[[(4-cyclohexylpiperazin-1-yl)acetyl]amino]propanamide, N-methyl-N-(3,4,5-trimethoxybenzyl)-3-(1H-indol-3-yl)-2-[[(4-cyclohexylpiperazin-1-yl)acetyl]amino]propanamide, N-methyl-N-(3,4,5-trimethylbenzyl)-3-(1H-indol-3-yl)-2-[[(4-cyclohexylpiperazin-1-yl )acetyl]amino]propanamide, N-methyl-N-(3,4,5-triethoxybenzyl)-3-(1H-indol-3-yl)-2-[[(4-cyclohexylpiperazin-1-yl)acetyl]amino]propanamide, N-methyl-N-(3,4,5-triethylbenzyl)- 3-(1H-indol-3-yl)-2-[[(4-cyclohexylpiperazin-1-yl)acetyl]amino]propanamide, N-methyl-N-(3,4,5-trichlorobenzyl)-3-(1H-indol-3-yl)-2-[[(4-cyclohexylpiperazin-1-yl)acetyl]amino]propanamide, N-[3,4,5-tri(trifluoromethyl)benzyl]-3-(1H-indol-3-yl)-2-[[(4-cyclohexylpiperazin-1-yl)acetyl]amino]propanamide, N-methyl-N-(2-methoxybenzyl)-3-(1H-indol-3-yl)-2-[[[4-(piperidin-1-yl)piperidin-1-yl]acetyl]amino]propanamide, N-methyl-N-(2-ethoxybenzyl)-3-(1H-indol-3-yl)-2-[[[4-(piperidin-1-yl)piperidin-1-yl]acetyl]amino]propanamide, N-methyl-N-(2-methylbenzyl)-3-(1H-indol-3-yl)-2-[[[4-(piperidin-1-yl)piperidin-1-yl]acetyl]amino]propanamide, N-methyl-N-(2-chlorobenzyl)-3-(1H-indol-3-yl)-2-[[[4-(piperidin-1-yl)piperidin-1-yl]acetyl]amino]propanamide, N-methyl-N-(2-trifluoromethylbenzyl)-3-(1H-indol-3-yl)-2-[[[4-(piperidin-1-yl)piperidin-1-yl]acetyl]amino]propanamide, N-methyl-N-(2-ethylbenzyl)-3-(1H-indol-3-yl)-2-[[[4-(piperidin-1-yl)piperidin-1-yl]acetyl]amino]propanamide, N-methyl-N-(3,4-dimethoxybenzyl)-3-(1H-indol-3-yl)-2-[[[4-(piperidin-1-yl)piperidin-1-yl]acetyl]amino]propanamide, N-methyl-N-(3,4-dimethylbenzyl)-3-(1H-indol-3-yl)-2-[[[4-(piperidin-1-yl)piperidin-1-yl]acetyl]amino]propanamide, N-methyl-N-(3,4-diethoxybenzyl)-3-(1H-indol-3-yl)-2-[[[4-(piperidin-1-yl)piperidin-1-yl]acetyl]amino]propanamide, N-methyl-N-(3,4-diethylbenzyl)-3-(1H-indol-3-yl)-2-[[[4-(piperidin-1-yl)piperidin-1-yl]acetyl]amino]propanamide, N-methyl-N-(3,4-dichlorobenzyl)-3-(1H-indol-3-yl)-2-[[[4-(piperidin-1-yl)piperidin-1-yl]acetyl]amino]propanamide, N-[3,5-bis(trifluoromethyl)benzyl]-3-(1H-indol-3-yl)-2-[[[4-(piperidin-1-yl)piperidin-1-yl]acetyl]amino]propanamide, N-methyl-N-(3,4,5-trimethoxybenzyl)-3-(1H-indol-3-yl)-2-[[[4-(piperidin-1-yl)piperidin-1-yl]acetyl]amino]

propanamide, N-methyl-N-(3,4,5-trimethylbenzyl)-3-(1H-indol-3-yl)-2-[[[4-(piperidin-1-yl)piperidin-1-yl]acetyl]amino]propanamide, N-methyl-N-(3,4,5-triethoxybenzyl)-3-(1H-indol-3-yl)-2-[[[4-(piperidin-1-yl)piperidin-1-yl]acetyl]amino]propanamide, N-methyl-N-(3,4,5-triethylbenzyl)-3-(1H-indol-3-yl)-2-[[[4-(piperidin-1-yl)piperidin-1-yl]acetyl]amino]propanamide, N-methyl-N-(3,4,5-trichlorobenzyl)-3-(1H-indol-3-yl)-2-[[[4-(piperidin-1-yl)piperidin-1-yl]acetyl]aminolpropanamide, and N-[3,4,5-tri(trifluoromethyl)benzyl]-3-(1H-indol-3-yl)-2-[[[4-(piperidin-1-yl)piperidin-1-yl]acetyl]amino]propanamide, or a pharmaceutically acceptable salt or solvate thereof.

7. A method as claimed in claim 1 employing a compound wherein $R^a$ and $R^b$ are taken together to form a carbonyl group, or a pharmaceutically acceptable salt or solvate thereof.

8. A method as claimed in claim 7 employing a compound wherein $R^1$ is hydrogen, methyl, or acetyl, or a pharmaceutically acceptable salt or solvate thereof.

9. A method as claimed in claim 8 employing a compound selected from the group consisting of N-(2-methoxybenzyl)-3-(1H-indol-3-yl)-2-[[(4-phenyl)-2,5-dioxopiperazin 1-yl]methyl]carbonyl]propanamide, N-(2-ethoxybenzyl)-3-(1H-indol-3-yl)-2-[[(4-phenyl)-2,5-dioxopiperazin-1-yl]methyl]carbonyl]propanamide, N-(2-methylbenzyl)-3-(1H-indol-3-yl)-2-[[(4-phenyl)-2,5-dioxopiperazin-1-yl]methyl]carbonyl]propanamide, N-(2-chlorobenzyl)-3-(1H-indol-3-yl)-2-[[(4-phenyl)-2,5-dioxopiperazin-1-yl]methyl]carbonyl]propanamide, N-(2-trifluoromethylbenzyl)-3-(1H-indol-3-yl)-2-[[(4-phenyl)-2,5-dioxopiperazin-1-yl]methyl]carbonyl]propanamide, N-(2-ethylbenzyl)-3-(1H-indol-3-yl)-2-[[(4-phenyl)-2,5-dioxopiperazin 1-yl]methyl]carbonyl]propanamide, N-(3,4-dimethoxybenzyl)-3-(1H-indol-3-yl)-2-[[(4-phenyl)-2,5-dioxopiperazin-1-yl]methyl]carbonyl]propanamide, N-(3,4-dimethylbenzyl)-3-(1H-indol-3-yl)-2-[[(4-phenyl)-2,5-dioxopiperazin-1-yl]methyl]carbonyl]propanamide, N-(3,4-diethoxybenzyl)-3-(1H-indol-3-yl)-2-[[(4-phenyl)-2,5-dioxopiperazin-1-yl]methyl]carbonyl]propanamide, N-(3,4-diethylbenzyl)-3-(1H-indol-3-yl)-2-[[(4-phenyl)-2,5-dioxopiperazin-1-yl]methyl]carbonyl]propanamide, N-(3,4-dichlorobenzyl)-3-(1H-indol-3-yl)-2-[[(4-phenyl)-2,5-dioxopiperazin 1-yl]methyl]carbonyl]propanamide, N-[3,5-bis(trifluoromethyl)benzyl]-3-(1H-indol-3-yl)-2-[[(4-phenyl)-2,5-dioxopiperazin-1-yl]methyl]carbonyl]propanamide, N-(3,4,5-trimethoxybenzyl)-3-(1H-indol-3-yl)-2-[[(4-phenyl)-2,5-dioxopiperazin-1-yl]methyl]carbonyl]propanamide, N-(3,4,5-trimethylbenzyl)-3-(1H-indol-3-yl)-2-[[[4-(phenyl)-2,5-dioxopiperazin-1-yl]methyl]carbonyl]propanamide, N-(3,4,5-triethoxybenzyl)-3-(1H-indol-3-yl)-2-[[(4-phenyl)-2,5-dioxopiperazin-1-yl]methyl]carbonyl]propanamnide, N-(3,4,5-triethylbenzyl)-3-(1H-indol-3-yl)-2-[[(4-phenyl)-2,5-dioxopiperazin-1-yl]methyl]carbonyl]propanamide, N-(3,4,5-trichlorobenzyl)-3-(1H-indol-3-yl)-2-[[(4-phenyl)-2,5-dioxopiperazin-1-yl]methyl]carbonyl]propanamide, and N-[3,4,5-tri(trifluoromethyl)benzyl]-3-(1H-indol-3-yl)-2-[[(4-phenyl)-2,5-dioxopiperazin-1-yl]methyl]carbonyl]propanamide, N-(2-methoxybenzyl)-3-(1H-indol-3-yl)-2-[[(4-methyl)-2,5-dioxopiperazin-1-yl]methyl]carbonyl]propanamide, N-(2-ethoxybenzyl)-3-(1H-indol-3-yl)-2-[[(4-methyl)-2,5-dioxopiperazin-1-yl]methyl]carbonyl]propanamide, N-(2-methylbenzyl)-3-(1H-indol-3-yl)-2-[[(4-methyl)-2,5-dioxopiperazin-1-yl]methyl]carbonyl]propanamide, N-(2-chlorobenzyl)-3-(1H-indol-3-yl)-2-[[(4-methyl)-2,5-dioxopiperazin-1-yl]methyl]carbonyl]propanamide, N-(2-trifluoromethylbenzyl)-3-(1H-indol-3-yl)-2-[[(4-methyl)-2,5-dioxopiperazin-1-yl]methyl]carbonyl]propanamide, N-(2-ethylbenzyl)-3-(1H-indol-3-yl)-2-[[(4-methyl)-2,5-dioxopiperazin-1-yl]methyl]carbonyl]propanamide, N-(3,4-dimethoxybenzyl)-3-(1H-indol-3-yl)-2-[[(4-methyl)-2,5-dioxopiperazin-1-yl]methyl]carbonyl]propanamide, N-(3,4-dimethylbenzyl)-3-(1H-indol-3-yl)-2- [[(4-methyl)-2,5-dioxopiperazin-1-yl]methyl]carbonyl]propanamide, N-(3,4-diethoxybenzyl)-3-(1H-indol-3-yl)-2-[[(4-methyl)-2,5-dioxopiperazin-1-yl]methyl]carbonyl]propanamide, N-(3,4-diethylbenzyl)-3-(1H-indol-3-yl)-2-[[(4-methyl)-2,5-dioxopiperazin-1-yl]methyl]carbonyl]propanamide, N-(3,4-dichlorobenzyl)-3-(1H-indol-3-yl)-2-[[(4-methyl)-2,5-dioxopiperazin-1-yl]methyl]carbonyl]propanamide, N-[3,5-bis(trifluoromethyl)benzyl]-3-(1H-indol-3-yl)-2-[[(4-methyl)-2,5-dioxopiperazin-1-yl]methyl]carbonyl]propanamide, N-(3,4,5-trimethoxybenzyl)-3-(1H-indol-3-yl)-2-[[(4-methyl)-2,5-dioxopiperazin-1-yl]methyl]carbonyl]propanamide, N-(3,4,5-trimethylbenzyl)-3-(1H-indol-3-yl)-2-[[(4-methyl)-2,5-dioxopiperazin-1-yl]methyl]carbonyl]propanamide, N-(3,4,5-triethoxybenzyl)-3-(1H-indol-3-yl)-2-[[(4-methyl)-2,5-dioxopiperazin-1-yl]methyl]carbonyl]propanamide, N-(3,4,5-triethylbenzyl)-3-(1H-indol-3-yl)- 2-[[(4-methyl)-2,5-dioxopiperazin-1-yl]methyl]carbonyl]propanamide, N-(3,4,5-trichlorobenzyl)-3-(1H-indol-3-yl)-2-[[(4-methyl)-2,5-dioxopiperazin-1-yl]methyl]carbonyl]propanamide, N-[3,4,5-tri(trifluoromethyl)benzyl]-3-(1H-indol-3-yl)-2-[[(4-methyl)-2,5-dioxopiperazin-1-yl]methyl]carbonyl]propanamide, N-(2-methoxybenzyl)-3-(1H-indol-3-yl)-2-[[(4-benzyl)-2,5-dioxopiperazin-1-yl]methyl]carbonyl]propanamide, N-(2-ethoxybenzyl)-3-(1H-indol-3-yl)-2-[[(4-benzyl)-2,5-dioxopiperazin-1-yl]methyl]carbonyl]propanamide, N-(2-methylbenzyl)-3-(1H-indol-3-yl)-2-[[(4-benzyl)-2,5-dioxopiperazin-1-yl]methyl]carbonyl]propanamide, N-(2-chlorobenzyl)-3-(1H-indol-3-yl)-2-[[(4-benzyl)-2,5-dioxopiperazin-1-yl]methyl]carbonyl]propanamide, N-(2-trifluoromethylbenzyl)-3-(1H-indol-3-yl)-2-[[(4-benzyl)-2,5-dioxopiperazin-1-yl]methyl]carbonyl]propanamide, N-(2-ethylbenzyl)-3-(1H-indol-3-yl)-2-[[(4-benzyl)-2,5-dioxopiperazin-1-yl]methyl]carbonyl]propanamide, N-(3,4-dimethoxybenzyl)-3-(1H-indol-3-yl)-2-[[(4-benzyl)-2,5-dioxopiperazin-1-yl]methyl]carbonyl]propanamide, N-(3,4-dimethylbenzyl)-3-(1H-indol-3-yl)-2-[[(4-benzyl)-2,5-dioxopiperazin-1-yl]methyl]carbonyl]propanamide, N-(3,4-diethoxybenzyl)-3-(1H-indol-3-yl)-2-[[(4-benzyl)-2,5-dioxopiperazin-1-yl]methyl]carbonyl]propanamide, N-(3,4-diethylbenzyl)-3-(1H-indol-3-yl)-2-[[(4-benzyl)-2,5-dioxopiperazin-1-yl]methyl]carbonyl]propanamide, N-(3,4-dichlorobenzyl)-3-(1H-indol-3-yl)-2-[[(4-benzyl)-2,5-dioxopiperazin-1-yl]methyl]carbonyl]propanamide, N-methyl-N-[3,5-bis(trifluoromethyl)benzyl]-3-(1H-indol-3-yl)-2-[[(4-benzyl)-2,5-dioxopiperazin-1-yl]methyl]carbonyl]propanamide, N-(3,4,5-trimethoxybenzyl)-3-(1H-indol-3-yl)-2-[[(4-benzyl )-2,5-dioxopiperazin-1-yl]methyl]carbonyl]propanamide, N-(3,4,5-trimethylbenzyl)-3-(1H-indol-3-yl)-2-[[(4-benzyl)-2,5-dioxopiperazin-1-yl]methyl]carbonyl]propanamide, N-(3,4,5-triethoxybenzyl)-3-(1H-indol-3-yl)-2-[[(4-benzyl)-2,5-dioxopiperazin-1-yl]methyl]carbonyl]propanamide, N-(3,4,5-triethylbenzyl)-3-(1H-indol-3-yl)-2-[[(4-benzyl)-2,5-dioxopiperazin-1-yl]methyl]carbonyl]propanamide, N-(3,4,5-trichlorobenzyl)-3-(1H-indol-3-yl)-2-[[(4-benzyl)-2,5-dioxopiperazin-1-yl]methyl]carbonyl]propanamide, and N-methyl-N-[3,4,5-tri(trifluoromethyl)benzyl]-3-(1H-indol-3-yl)-2-[[(4-benzyl)-2,5-dioxopiperazin-1-yl]methyl]carbonyl]propanamide, or a pharmaceutically acceptable salt or solvate thereof.

\* \* \* \* \*